United States Patent
Morrow et al.

(10) Patent No.: US 11,246,949 B2
(45) Date of Patent: Feb. 15, 2022

(54) IMAGING CONTRAST AGENTS AND USES THEREOF

(75) Inventors: Janet R. Morrow, Williamsville, NY (US); Pavel Tsitovich, Amherst, NY (US); Sarina Dorazio, Elba, NY (US); Abiola Olatunde, Amherst, NY (US)

(73) Assignee: The Research Foundation for The State University of New York, Amherst, NY (US)

( * ) Notice: Subject to any disclaimer, the term of this patent is extended or adjusted under 35 U.S.C. 154(b) by 9 days.

(21) Appl. No.: 14/116,270

(22) PCT Filed: May 11, 2012

(86) PCT No.: PCT/US2012/037590
§ 371 (c)(1),
(2), (4) Date: Mar. 17, 2014

(87) PCT Pub. No.: WO2012/155076
PCT Pub. Date: Nov. 15, 2012

(65) Prior Publication Data
US 2014/0193344 A1    Jul. 10, 2014

Related U.S. Application Data

(60) Provisional application No. 61/583,967, filed on Jan. 6, 2012, provisional application No. 61/583,039, filed on Jan. 4, 2012, provisional application No. 61/484,873, filed on May 11, 2011.

(51) Int. Cl.
| | | |
|---|---|---|
| A61B 5/055 | (2006.01) | |
| A61K 49/10 | (2006.01) | |
| C07D 213/74 | (2006.01) | |
| C07D 213/58 | (2006.01) | |
| C07D 213/59 | (2006.01) | |
| G01N 33/52 | (2006.01) | |
| C07D 213/53 | (2006.01) | |
| C07D 213/68 | (2006.01) | |
| C07D 471/04 | (2006.01) | |

(52) U.S. Cl.
CPC .......... *A61K 49/106* (2013.01); *C07D 213/53* (2013.01); *C07D 213/58* (2013.01); *C07D 213/59* (2013.01); *C07D 213/68* (2013.01); *C07D 213/74* (2013.01); *C07D 471/04* (2013.01); *G01N 33/52* (2013.01)

(58) Field of Classification Search
CPC .................................................. A61K 49/106
USPC .................................................... 424/9.363
See application file for complete search history.

(56) References Cited

U.S. PATENT DOCUMENTS

| | | | |
|---|---|---|---|
| 4,657,903 A | | 4/1987 | Scovill et al. |
| 5,312,617 A | * | 5/1994 | Unger .................. A61K 49/06 424/9.321 |
| 8,518,373 B2 | | 8/2013 | Aime et al. |
| 2002/0010120 A1 | * | 1/2002 | Hage .................. C07F 11/005 510/302 |
| 2002/0127182 A1 | * | 9/2002 | Sherry ................ A61K 49/106 424/9.363 |
| 2003/0129579 A1 | | 7/2003 | Bornhop et al. |
| 2005/0191243 A1 | | 9/2005 | Aime et al. |
| 2006/0057071 A1 | | 3/2006 | Wong et al. |
| 2006/0275217 A1 | * | 12/2006 | Caravan ............... A61K 49/085 424/9.363 |
| 2007/0218010 A1 | * | 9/2007 | Hasserodt ........... A61K 49/085 424/9.363 |
| 2008/0241074 A1 | | 10/2008 | Bornhop et al. |
| 2009/0142273 A1 | | 6/2009 | Pagel et al. |
| 2011/0076237 A1 | * | 3/2011 | Grimmond .......... A61K 49/103 424/9.364 |

FOREIGN PATENT DOCUMENTS

| | | | | |
|---|---|---|---|---|
| WO | WO-2006032705 A2 | * | 3/2006 | ......... A61K 49/1812 |
| WO | WO 2009080138 A2 | * | 7/2009 | |

OTHER PUBLICATIONS

Muller et al. J. Am. Chem. Soc. 2003, 125, 8405-8407.*
Mandal et al. Inorg,. Chem. 1997, 36, 5424-5425.*
Zhang et al. J. Am. Chem. Soc. 2005, 127, 17572-17573.*
Himmelreich et al. Methods 2009, 48, 112-124.*
Weyhermuller et al. J. CHem. Soc. Dalton Trans. 1998, 3805-3813.*
Rodriquez et al. J. Pharm. Sci. 2008, 3637-2665.*
Bu et al. Polyhedron 2000, 431-435.*
Hajj et al. Inorg. Chem. 2009, 48, 10416-10423.*
Liu et al. Chin. J. Chem. 1998, 16, 16-21.*
Di Vaira et al. J. Chem. Soc., Dalton Trans. 1996, 2679-2684.*
Norante et al. Inorg. Chem. 1990, 29, 2822-2829. (Year: 1990).*
Farrugia et al. Acta Cryt. 1991, C47, 1312-1313. (Year: 1991).*
Dunand et al. Chem. Eur. J. 2001, 7, 5160-5167.I (Year: 2001).*
Kasuga et al., Synthesis, structural characterization and antimicrobial activities of 12 zinc(II) complexes with four thiosemicarbazone and two semicarbazone ligands, Journal of Inorganic Biochemistry, 2003, vol. 96, pp. 298-310.

(Continued)

*Primary Examiner* — Michael G. Hartley
*Assistant Examiner* — Sean R Donohue
(74) *Attorney, Agent, or Firm* — Hodgson Russ LLP

(57) ABSTRACT

Provided are macrocyclic compounds having a macrocyclic core which has at least one macrocyclic donor and at least one pendant group which has at least one donor group. The macrocyclic compounds can be complexed to Fe(II) and Ni(II). The macrocyclic compounds can be used in imaging methods. For example, the compounds can be used MRI paraCEST contrast agents.

11 Claims, 24 Drawing Sheets

(56) References Cited

OTHER PUBLICATIONS

De Sousa et al., Crystallographic and Mossbauer Spectroscopic Applications in Dependence of Partial Quadrupole Slitting, [R], on the C—Sn—C Angle in Seven-Coordinated Diorganotin(IV) Complexes, Inorganic Chemistry, Apr. 25, 2006, vol. 45, pp. 4518-4525.
Kowol et al., Effect of metal ion complexation and chalcogen donor identity on the antiproliferative activity of 2-acetylpyridine N,N-dimethyl(chalcogen)semicarbazones, Journal of Inorganic Biochemistry, Jul. 31, 2007, vol. 101, pp. 1946-1957.
Kowol et al., Impact of Metal Coordination of Cytotoxicity of 3-Aminopyridine-2-carboxaldehyde Thiosemicarbazone (Triapine) and Novel Insights into Terminal Dimethylation, Journal of Medicinal Chemistry, Jul. 28, 2009, vol. 52, No. 16, pp. 5032-5043.
Linert et al., Chromotropism Behavior and Biological Activity of some Schiff Base-Mixed Ligand Transition Metal complexes, Synthesis and Reactivity in Inorganic, Metal-Organic, and Nano-Metal Chemistry, 39, 570-599, 2009.
Keppler et al., Impact of Metal Coordination on Cytotoxicity of 3-Aminopyridine-2-carboxaldehyde Thiosemicarbazone (Triapine) and Novel Insights into Terminal Dimethylation, J. Med. Chem. 2009, 52, 5032-5043, Jul. 28, 2009.

\* cited by examiner

IMAGING CONTRAST AGENTS AND USES THEREOF

CROSS-REFERENCE TO RELATED APPLICATIONS

This application claims priority to U.S. provisional patent application No. 61/484,873, filed May 11, 2011, U.S. provisional patent application No. 61/583,039, filed Jan. 4, 2012, and U.S. provisional patent application No. 61/583,967, filed Jan. 6, 2012, the disclosures of which are incorporated herein by reference.

FIELD OF THE INVENTION

The present invention generally relates to macrocyclic compounds that can be used as contrast agents. In particular, the present invention relates to macrocyclic contrast agents for use in magnetic resonance imaging methods.

BACKGROUND OF THE INVENTION

One of the most powerful and non-invasive tools that clinicians utilize in order to gain insight into the structural or physiological functions of changes within an individual is Magnetic Resonance Imaging (MRI). This tool that allows a specialized magnetic reader to detect and measure proton relaxation signals that can be varied by contrast agents, which have been predigested or pre-injected into the body and localized within an individual, is of interest. Such contrast agents are a key component of determining the ultimate sensitivity of the MRI image.

BRIEF SUMMARY OF THE INVENTION

In an aspect, the present invention provides a macrocyclic compound having at least one heteroatom and at least one pendant donor as a substituent of the macrocyclic core. Any of the macrocyclic compounds disclosed herein can be Fe(II) or Ni(II) complexes. In an embodiment, the present invention provides a macrocyclic compound having at least one exchangeable proton having a macrocyclic core having from 9 to 15 atoms where at least one of the atoms in the macrocyclic core is a N atom. At least two carbon atoms separate a heteroatom selected from the group consisting of: N atom, O atom, or S atom. The compound has at least one substituent (i.e., pendant group) having at least one pendant donor on the macrocyclic core.

In an aspect, the present invention provides imaging methods using the macrocyclic compounds. The imaging methods use magnetic resonance imaging methods. Examples of such methods include, Magnetic Resonance Imaging (MRI) and Magnetic Resonance Spectroscopic Imaging (MRSI)

The imaging methods of the present invention can be used to image a cell, organ, vasculature, tissue, or a part thereof. The cell, organ, vasculature, tissue can be part of an individual. The In an embodiment, the invention provides a method to obtain an image of at least a portion of a cell, organ, vasculature, or tissue comprising the steps of: contacting a cell, organ, or tissue with the compounds of the invention, and imaging at least a portion of the cell, organ, or tissue to obtain an image of the portion of cell, organ, or tissue.

DETAILED DESCRIPTION OF THE INVENTION

Figure 1:
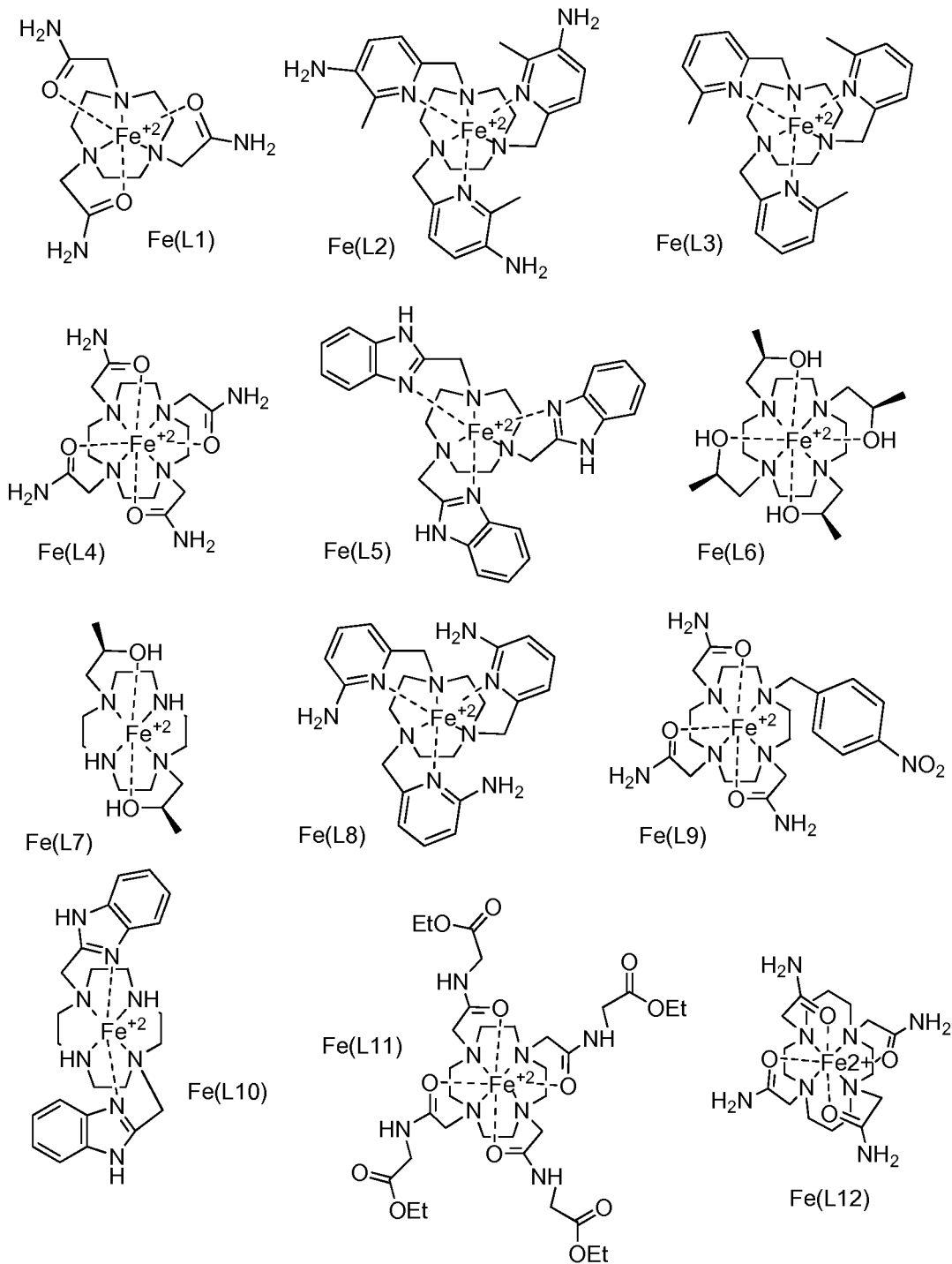
FIG. 1. Examples of Fe(II) macrocyclic compounds of the present disclosure featuring exchangeable NH or OH groups.

The present invention provides macrocyclic compounds having a variety of core structures and a variety of substituents on the macrocyclic core. The macrocyclic compounds can be complexed to Fe(II) or Ni(II). For example, the macrocyclic compounds can be used in imaging applications.

The macrocyclic compounds of the present invention (which can be complexed to Fe(II) or Ni(II)) can be used as paraCEST MRI contrast agents or are paramagnetic complexes for magnetic resonance spectroscopy. These complexes may have properties that change with pH and temperature and so can be used as pH and temperature dependent sensors. There are several advantages of using Fe(II) and Ni(II) transition metal ion complexes of the macrocyclic compounds including 1) favorable paramagnetic properties, 2) versatile coordination chemistry that allows us to use a larger variation of donor groups, 3) biological relevance of some transition metal ions in the body with the potential of making safer contrast agents. It is desirable to control certain properties of the Fe(II) or Ni(II) metal ion including 1) oxidation state, 2) spin state, 3) dynamic nature of the macrocyclic ligand, 4) reactivity of the metal ion complex toward dissociation of the metal ion and 5) reactivity of the metal ion complex toward biologically relevant anions such as carbonate and phosphate as well as with oxygen. These points are elaborated on below.

For both paraCEST and MRS applications, it is desirable that the paramagnetic metal ion complexes produce highly shifted proton resonances that have relatively narrow linewidths. Fe(II) and Ni(II) have short electronic relaxation times (10-11 to 10-12 s−1) and favorable paramagnetic properties for producing large proton shifts. Fe(II) and Ni(II) ions have the advantage that paramagnetic shift contributions arise through both contact (through-bond) and pseudo-contact (dipolar, through-space) mechanisms. This can result in highly dispersed proton shifts for the Fe(II) and Ni(II) transition metal ion macrocycle complexes.

An important advantage is the diverse coordination chemistry of Fe(II) and Ni(II) transition metal ions. In other words, there are a variety of potential ligand donor groups that bind tightly to Fe(II) and Ni(II) including the heterocyclic donor groups of the present invention. These donor groups can facilitate the design of contrast agents with favorable contrast properties as well as the design of smart contrast agents that are responsive to pH and other environmental factors.

Another advantage is that iron is an endogenous metal ion. The human body has mechanisms for handling excess iron, were the complex to dissociate in the body. Thus the Fe(II) contrast agents may be safer to use in patients that cannot tolerate Gd(III) contrast agents.

There were many challenges that had to be overcome in the design of the Fe(II) and Ni(II) contrast agents. First, ligands were chosen to stabilize the high spin (paramagnetic) states of Fe(II) (S=2) and Ni(II) (S=1). Both metal ions have low spin states that are diamagnetic and thus would not function as paramagnetic MRI contrast agents. For Ni(II), we avoided macrocycles that would allow a square planar geometry and give diamagnetic Ni(II). Second, the divalent oxidation state had to be stabilized. This was accomplished by using neutral ligands that strongly stabilize the Fe(II) or Ni(II) oxidation state.

Further challenges include controlling the coordination geometry and the dynamic nature of the macrocyclic complex. For Fe(II), six, seven or eight coordinate complexes are most suitable. Fe(L1) is an example of a complex that is six coordinate. However, to our surprise, macrocycles with eight donor groups such as the tetrasubstituted cyclen macrocycles formed complexes with Fe(II) that appear to have all of the pendent groups coordinated to form an eight coordinate complex. Ni(II), by contrast, can be four, five, six or seven coordinate in the complexes described herein. The coordination geometry is important in this case because five and six coordinate Ni(II) complexes are known to have shorter electronic relaxation times and narrower proton resonances, which can be desirable. The dynamic nature of the macrocyclic complexes on the proton NMR time scale is a consideration. For MRS, it is desirable the protons on the methylenes of the macrocycle be sharp and not broadened by dynamic rearrangement of the macrocycle. For paraCEST, it is desirable only the exchangeable NH or OH protons be sharp. Thus, contrast agents for MRS in particular are facilitated by the incorporation of rigid pendent groups into the macrocyclic complex to slow down dynamic processes such as ring flipping and pendent group reorientation. The barrier to dynamic macrocycle-based processes that we have observed for Fe(II) and Ni(II) complexes was surprisingly low. Pyridine pendents worked surprisingly well in arresting the dynamic process. Other unanticipated developments include the fact that the exchangeable protons can be sharp and not affected by dynamic processes that affect the macrocycle CH protons. For example, most Fe(II) or Ni(II) complexes of macrocycles containing amide pendent groups had sharp NH resonances due to the amide groups that lead to a strong paraCEST peak, but very broad CH proton resonances due to a fluxional macrocycle backbone.

Additionally, there are advantages to encapsulating the Fe(II) ion in a macrocycle with high denticity so that there are no available coordination sites for binding small molecules. This has advantages in imaging because biologically relevant anions such as phosphate or carbonate cannot coordinate to the metal ion. If the anions did coordinate, the contrast properties would change because the proton resonances would be influenced. In addition, the reaction of the complexes with oxygen or peroxide is inhibited because these molecules cannot coordinate to the metal ion. It was surprising that Fe(II) and Ni(II) complexes of the present invention can have a large degree of kinetic inertness towards dissociation as well as a large degree of thermodynamic stability. This is shown by their extremely slow dissociation in the presence of acid or excess concentrations of Zn(II) or Cu(II) or large biologically relevant concentrations of carbonate (25 mM) and phosphate (0.4 mM).

In an aspect, the present invention provides a macrocyclic compound having at least one heteroatom and at least one pendent donor as a substituent of the macrocyclic core. Any of the macrocyclic compounds disclosed herein can be Fe(II) or Ni(II) complexes.

In an embodiment, the present invention provides a macrocyclic compound having a macrocyclic core having from 9 to 15 atoms where at least one of the atoms in the macrocyclic core is a N atom. At least two carbon atoms separate a heteroatom selected from the group consisting of: N atom, O atom, or S atom. The compound has at least one substituent (i.e., pendant group) on the macrocyclic core.

The pendant group has at least one pendant donor. For example the pendant group can have the following structure:

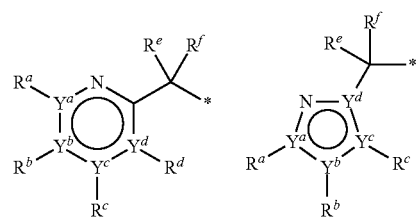

These pendant groups are covalently attached to a macrocyclic core (e.g., at a nitrogen) at the asterisk sign. These heterocycles can be comprised of six-atom aromatic ring with at least one N atom, or five-atom aromatic ring with at least one N atom. $R^e$=H, Me, Et, Pr, i-Pr, t-Butyl, linear or branched alkyl $C_1$-$C_{12}$, PEG. $R^f$=H, Me, Et, Pr, i-Pr, t-Butyl, linear or branched alkyl $C_1$-$C_{12}$, PEG.

For six-atom ring: $Y^a$=C or N, $Y^b$=C or N, $Y^c$=C or N, $Y^d$=C or N. For five-atom ring: $Y^a$=C or N; $Y^b$=C, N, O, or S; $Y^c$=C, N, O, or S; $Y^d$=C or N. For six-atom ring if $Y^a$=N, then $R^a$ is null; if $Y^b$=N, then $R^b$ is null; if $Y^c$=N, then $R^e$ is null; if $Y^d$=N, then $R^d$ is null.

For six-atom ring if $Y^a$=C, then $R^a$=H, Me, Et, Pr, i-Pr, t-Butyl, linear or branched alkyl $C_1$-$C_{12}$, PEG, —CCH, Ph, substituted Ph, —CF$_3$, —CN, —CH$_2$Cl, —CH$_2$F, —CHF$_2$, —OH, —OMe, —OEt, —OPr, —OiPr, —OCF$_3$, —CH$_2$OH, —CH$_2$OMe, —CH(OH)Me, —CH(OH)Et, —C(OH)Me$_2$, —CH$_2$NH$_2$, —CH$_2$NHMe, —CH(NH$_2$)Me, —CH(NH$_2$)Et, —C(NH$_2$)Me$_2$, —B(OH)$_2$, —NH$_2$, —NHMe, —NHEt, —NHPr, —NMe$_2$, —SH, —SMe, —SEt, —NO$_2$, —NHSO$_2$Me, —(CO)NH$_2$, —(CO)NHMe, —(CO)NMe$_2$, —COOMe, —COOEt, —COOOH, —COMe, Ar, substituted Ar, heterocycle.

For six-atom ring if $Y^b$=C, then $R^b$=H, Me, Et, Pr, i-Pr, t-Butyl, linear or branched alkyl $C_1$-$C_{12}$, PEG, —CCH, Ph, substituted Ph, —CF$_3$, —CN, —CH$_2$Cl, —CH$_2$F, —CHF$_2$, —OH, —OMe, —OEt, —OPr, —OiPr, —OCF$_3$, —CH$_2$OH, —CH$_2$OMe, —CH(OH)Me, —CH(OH)Et, —C(OH)Me$_2$, —CH$_2$NH$_2$, —CH$_2$NHMe, —CH(NH$_2$)Me, —CH(NH$_2$)Et, —C(NH$_2$)Me$_2$, —B(OH)$_2$, —NH$_2$, —NHMe, —NHEt, —NHPr, —NMe$_2$, —SH, —SMe, —SEt, —NO$_2$, —NHSO$_2$Me, —(CO)NH$_2$, —(CO)NHMe, —(CO)NMe$_2$, —COOMe, —COOEt, —COOOH, —COMe, Ar, substituted Ar, heterocycle.

For six-atom ring if $Y^c$=C, then $R^c$=H, Me, Et, Pr, i-Pr, t-Butyl, linear or branched alkyl $C_1$-$C_{12}$, PEG, —CCH, Ph, substituted Ph, —CF$_3$, —CN, —CH$_2$Cl, —CH$_2$F, —CHF$_2$, —OH, —OMe, —OEt, —OPr, —OiPr, —OCF$_3$, —CH$_2$OH, —CH$_2$OMe, —CH(OH)Me, —CH(OH)Et, —C(OH)Me$_2$, —CH$_2$NH$_2$, —CH$_2$NHMe, —CH(NH$_2$)Me, —CH(NH$_2$)Et, —C(NH$_2$)Me$_2$, —B(OH)$_2$, —NH$_2$, —NHMe, —NHEt, —NHPr, —NMe$_2$, —SH, —SMe, —SEt, —NO$_2$, —NHSO$_2$Me, —(CO)NH$_2$, —(CO)NHMe, —(CO)NMe$_2$, —COOMe, —COOEt, —COOOH, —COMe, Ar, substituted Ar, heterocycle.

For six-atom ring if $Y^d$=C, then $R^d$=H, Me, Et, Pr, i-Pr, t-Butyl, linear or branched alkyl $C_1$-$C_{12}$, PEG, —CCH, Ph, substituted Ph, —$CF_3$, —CN, —$CH_2Cl$, —$CH_2F$, —$CHF_2$, —OH, —OMe, —OEt, —OPr, —OiPr, —$OCF_3$, —$CH_2OH$, —$CH_2OMe$, —CH(OH)Me, —CH(OH)Et, —C(OH)$Me_2$, —$CH_2NH_2$, —$CH_2NHMe$, —CH($NH_2$)Me, —CH($NH_2$)Et, —C($NH_2$)$Me_2$, —B(OH)$_2$, —$NH_2$, —NHMe, —NHEt, —NHPr, —$NMe_2$, —SH, —SMe, —SEt, —$NO_2$, —$NHSO_2Me$, —(CO)$NH_2$, —(CO)NHMe, —(CO)$NMe_2$, —COOMe, —COOEt, —COOOH, —COMe, Ar, substituted Ar, heterocycle.

For five-atom ring if $Y^a$=S or O, then $R^a$ is null; if $Y^b$=S or O, then $R^b$ is null; if $Y^c$=S or O, then $R^c$ is null; if $Y^d$=S or O, then $R^d$ is null.

For five-atom ring if $Y^a$=C, then $R^a$=H, Me, Et, Pr, i-Pr, t-Butyl, linear or branched alkyl $C_1$-$C_{12}$, PEG, —CCH, Ph, substituted Ph, —$CF_3$, —CN, —$CH_2Cl$, —$CH_2F$, —$CHF_2$, —OH, —OMe, —OEt, —OPr, —OiPr, —$OCF_3$, —$CH_2OH$, —$CH_2OMe$, —CH(OH)Me, —CH(OH)Et, —C(OH)$Me_2$, —$CH_2NH_2$, —$CH_2NHMe$, —CH($NH_2$)Me, —CH($NH_2$)Et, —C($NH_2$)$Me_2$, —B(OH)$_2$, —$NH_2$, —NHMe, —NHEt, —NHPr, —$NMe_2$, —SH, —SMe, —SEt, —$NO_2$, —$NHSO_2Me$, —(CO)$NH_2$, —(CO)NHMe, —(CO)$NMe_2$, —COOMe, —COOEt, —COOOH, —COMe, Ar, substituted Ar, heterocycle.

For five-atom ring if $Y^b$=C, then $R^b$=H, Me, Et, Pr, i-Pr, t-Butyl, linear or branched alkyl $C_1$-$C_{12}$, PEG, —CCH, Ph, substituted Ph, —$CF_3$, —CN, —$CH_2Cl$, —$CH_2F$, —$CHF_2$, —OH, —OMe, —OEt, —OPr, —OiPr, —$OCF_3$, —$CH_2OH$, —$CH_2OMe$, —CH(OH)Me, —CH(OH)Et, —C(OH)$Me_2$, —$CH_2NH_2$, —$CH_2NHMe$, —CH($NH_2$)Me, —CH($NH_2$)Et, —C($NH_2$)$Me_2$, —B(OH)$_2$, —$NH_2$, —NHMe, —NHEt, —NHPr, —$NMe_2$, —SH, —SMe, —SEt, —$NO_2$, —$NHSO_2Me$, —(CO)$NH_2$, —(CO)NHMe, —(CO)$NMe_2$, —COOMe, —COOEt, —COOOH, —COMe, Ar, substituted Ar, heterocycle.

For five-atom ring if $Y^c$=C, then $R^c$=H, Me, Et, Pr, i-Pr, t-Butyl, linear or branched alkyl $C_1$-$C_{12}$, PEG, —CCH, Ph, substituted Ph, —$CF_3$, —CN, —$CH_2Cl$, —$CH_2F$, —$CHF_2$, —OH, —OMe, —OEt, —OPr, —OiPr, —$OCF_3$, —$CH_2OH$, —$CH_2OMe$, —CH(OH)Me, —CH(OH)Et, —C(OH)$Me_2$, —$CH_2NH_2$, —$CH_2NHMe$, —CH($NH_2$)Me, —CH($NH_2$)Et, —C($NH_2$)$Me_2$, —B(OH)$_2$, —$NH_2$, —NHMe, —NHEt, —NHPr, —$NMe_2$, —SH, —SMe, —SEt, —$NO_2$, —$NHSO_2Me$, —(CO)$NH_2$, —(CO)NHMe, —(CO)$NMe_2$, —COOMe, —COOEt, —COOOH, —COMe, Ar, substituted Ar, heterocycle.

For five-atom ring if $Y^a$=N, then $R^a$=H, Me, Et, Pr, i-Pr, t-Butyl, linear or branched alkyl $C_1$-$C_{12}$, PEG, —CCH, Ph, substituted Ph, —COMe, Ar, substituted Ar, heterocycle, or null.

For five-atom ring if $Y^b$=N, then $R^b$=H, Me, Et, Pr, i-Pr, t-Butyl, linear or branched alkyl $C_1$-$C_{12}$, PEG, —CCH, Ph, substituted Ph, —COMe, Ar, substituted Ar, heterocycle, or null.

For five-atom ring if $Y^c$=N, then $R^c$=H, Me, Et, Pr, i-Pr, t-Butyl, linear or branched alkyl $C_1$-$C_{12}$, PEG, —CCH, Ph, substituted Ph, —COMe, Ar, substituted Ar, heterocycle, or null.

Examples of suitable pendant groups include:

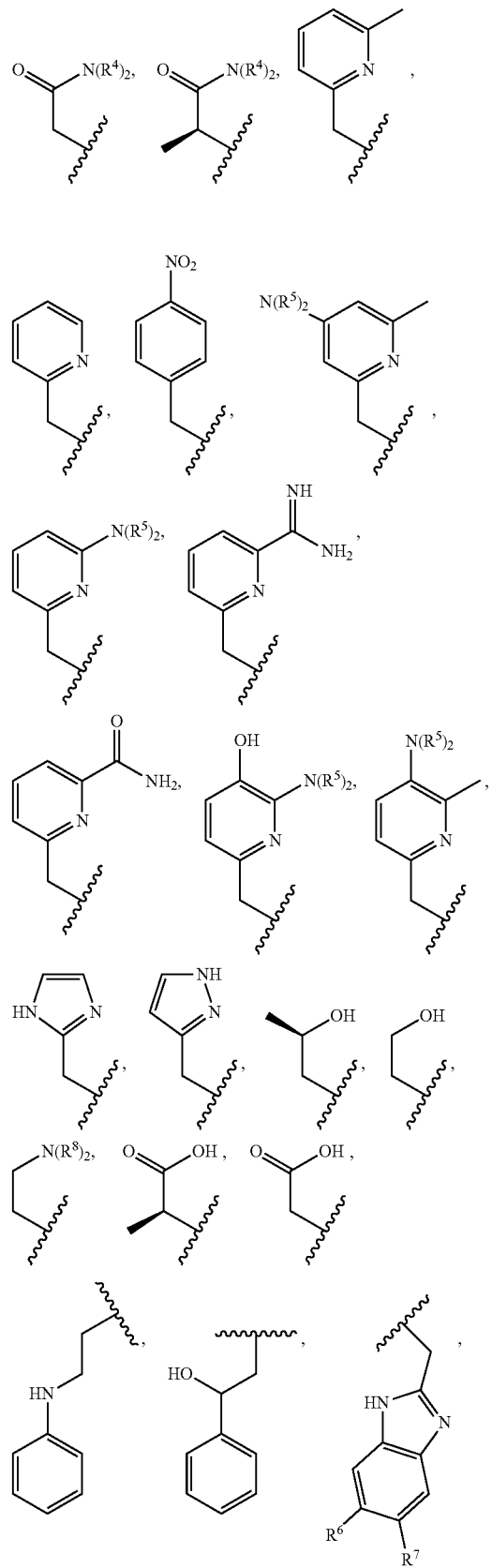

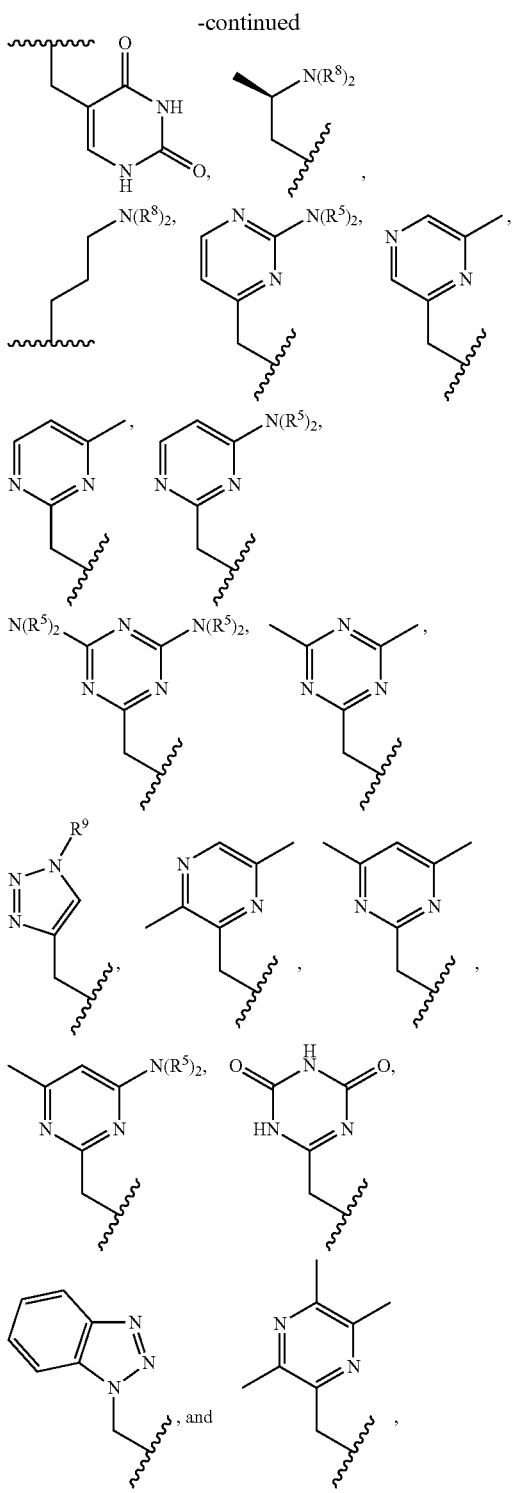

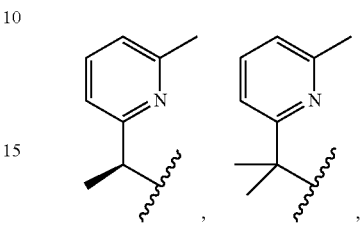

where each $R^4$ is independently selected from H, $C_1$ to $C_{12}$ alkyl group, PEG group ($-(O-CH_2CH_2-)_nOR$, where R is H or alkyl and n=1 to 12), thioether group ($-(S-CH_2CH_2)_nSR$, where R is H or alkyl and n=1-12), or $CH_2CO_2R^8$, each $R^5$ is independently selected from H, $C_1$ to $C_{12}$ alkyl group, PEG group ($-(O-CH_2CH_2-)_n$ OR, where R is H or alkyl and n=1 to 12), thioether group ($-(S-CH_2CH_2)_nSR$, where R is H or alkyl and n=1-12), $CH_2CO_2R^8$ or $OCH_3$, $R^6$ is H or $OCH_3$, $R^7$ is H, $OCH_3$, or $CO_2H$, and each $R^8$ and $R^9$ is independently selected from H, $C_1$ to $C_{12}$ alkyl group, PEG group ($-(O-CH_2CH_2-)_nOR$, where R is H or alkyl and n=1 to 12), thioether group ($-(S-CH_2CH_2)_nSR$, where R is H or alkyl and n=1-12). The macrocyclic compound has at least one exchangeable proton. Optionally, a Fe(II) or Ni(II) cation is complexed to the macrocyclic compound.

The pendant groups can be further substituted at the benzylic position (e.g.,

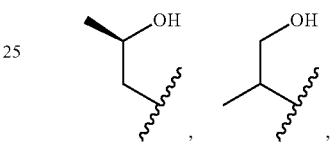

etc.), or any part of the alkyl group leading to the heteroatom (e.g.,

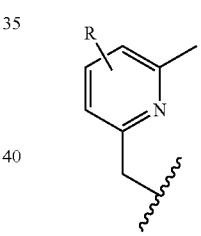

etc.), with a $C_1$ to $C_2$ alkyl group, and the group can be chiral or achiral. The substituents can be further substituted on the heterocyclic ring with, for example, where R is $-OCH_3$, $-OC_2H_5$, $C_1$ to $C_{12}$ alkyl groups of linear or branched structure, PEG group ($-(O-CH_2CH_2-)_nOR$, where R is H or alkyl and n=1 to 12), thioether group ($-(S-CH_2CH_2)_nSR$, where R is H or alkyl and n=1-12), $COOCH_3$, $COOCH_2CH_3$, and the group can be chiral or achiral.

The macrocyclic core is part of the macrocyclic compound. The macrocyclic core has a ring structure comprising carbon atoms and at least one heteroatom (e.g., N atom, O atom, or S atom). In various examples, the macrocyclic core can have 1, 2, 3, 4, 5 nitrogen atoms, 1, 2, 3, 4 oxygen atoms, can have 1, 2, 3, 4 sulfur atoms. The macrocyclic core can have a combination of different heteroatoms. For example, the macrocyclic core can have 6, 7, 8, 9, 10 carbons. For example, the macrocyclic core has from 9 to 15 atoms where at least one of the atoms in the macrocyclic core is a N atom. In various examples, there are two carbon atoms separating the heteroatoms in the macrocyclic core, there are three carbon atoms separating the heteroatoms in the macrocyclic core, or there is a combination of two carbons and three carbons separating the heteroatoms in the macrocyclic core. The one or more carbons in the macrocyclic core can be unsubstituted (e.g., $-CH_2-$) or can be substituted (e.g., —CHR—, or —CR$_2$—). For example, they can be substituted with the substituents disclosed herein.
Examples of suitable macrocyclic compounds include:
(I)
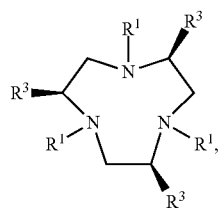
(II)
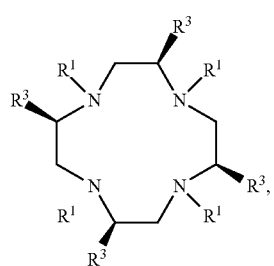
(III)
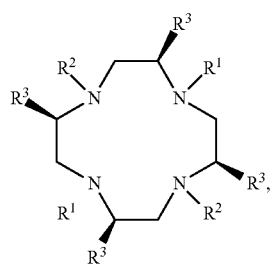
(IV)
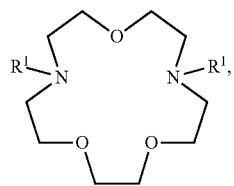
(V)
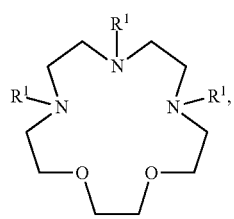
(VI)
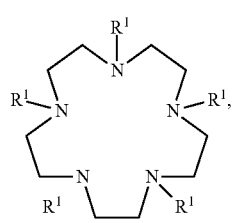
(VII)
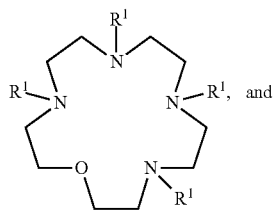
and
(VIII)
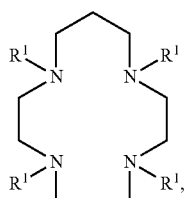
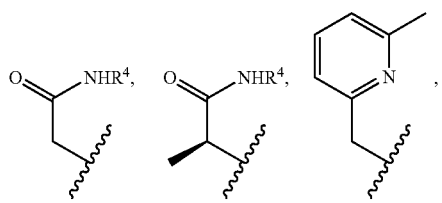
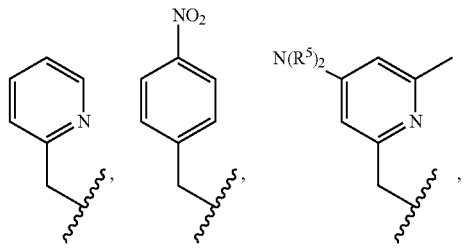
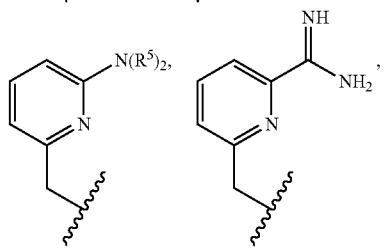
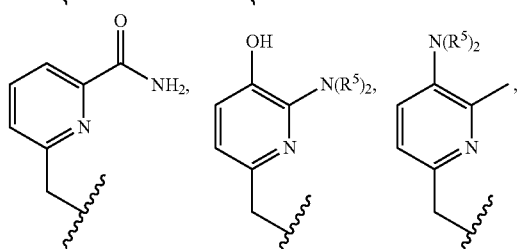
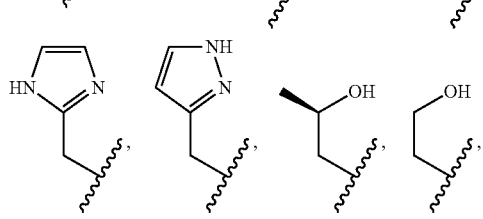

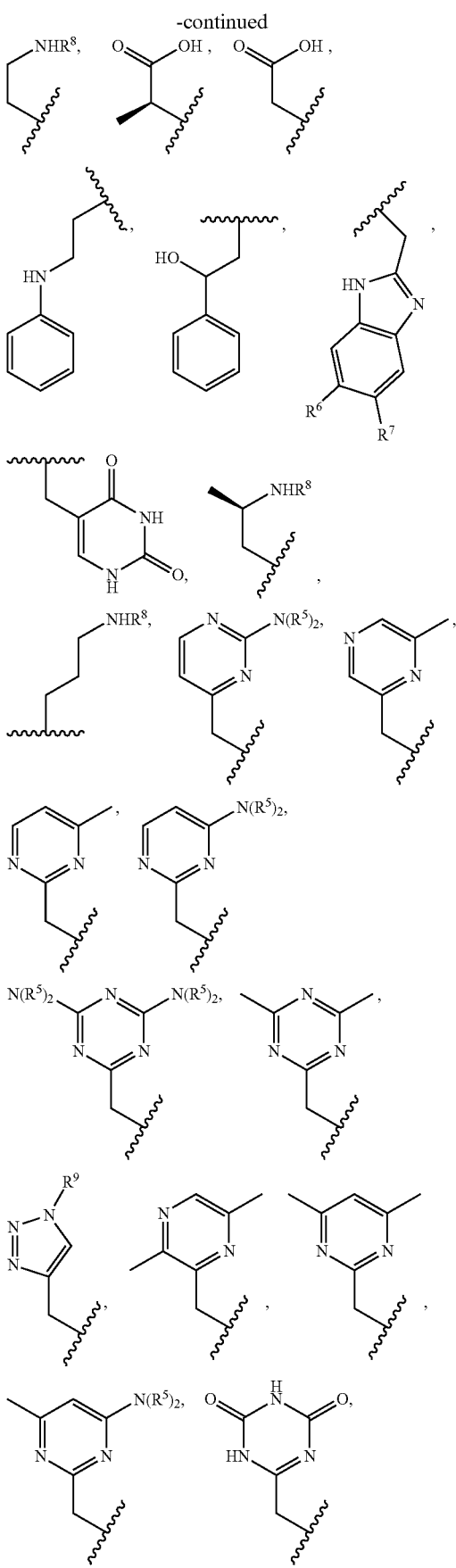

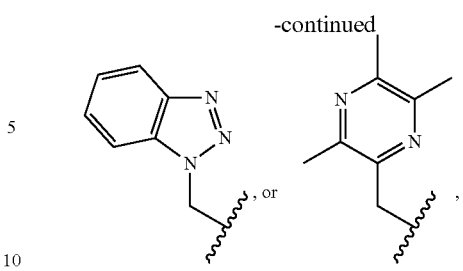

where each $R^1$ is independently selected from H, $CH_3$, each $R^2$ is independently selected from H or $CH_3$, and each $R^3$ is independently selected from H or $CH_3$. In an embodiment, $R^1$ is as defined herein, $R^2$ is H or $CH_3$ and $R^3$ is H or $CH_3$.

As used herein unless expressly defined otherwise, "alkyl group" refers to branched or unbranched saturated hydrocarbons. Examples of such alkyl groups include methyl groups, ethyl groups, butyl groups, nonyl groups, neopentyl groups, and the like. For example, the alkyl group can be a $C_1$ to $C_{12}$ alkyl-group, including all integer numbers of carbons and ranges of numbers of carbons therebetween. The alkyl group can be unsubstituted or substituted as described herein. For example, the alkyl group can be substituted with halogens (e.g., —F, —Cl, —Br, and —I), alcohols, amines, and esters.

As used herein, "macrocycle donor" refers to a heteroatom with an available lone pair of electrons to donate to a Fe(II) or Ni(II) center which is present in the macrocyclic core of the compound. For example, the macrocycle donor can be a nitrogen atom (e.g., a tertiary amine, a secondary amine), an oxygen atom (e.g., an ether), or sulfur atom (e.g., sulfane).

As used herein, "pendant donor" refers to a heteroatom with an available lone pair of electrons to donate to a Fe(II) or Ni(II) center, where the pendant donor is present in the pendant donor group substituents on the macrocyclic core of the compound. For example, the pendant donor can be a nitrogen atom (e.g., pyridine nitrogen, amide nitrogen, benzimidazole nitrogen, imidazole nitrogen, amino nitrogen, pyrazole nitrogen, imidamide nitrogen, aniline nitrogen, pyrazine nitrogen, triazine nitrogen, triazole nitrogen, pyrimidine nitrogen, benzotriazole nitrogen, triazinedione nitrogen, and the like), an oxygen atom (e.g., ketone oxygen, ester oxygen, alcohol oxygen, carboxylic acid oxygen, and the like), or a sulfur atom (e.g., thiol sulfur).

The macrocyclic compounds of the present invention can be prepared, for example, as described in FIGS. 3, 29, 30, 35, 36, 38, and the Examples. Modifications of these methods to provide modified compounds is within the purview of one having skill in the art.

In an embodiment, the present invention provides an orthogonal protection strategy using different protecting groups (e.g., Cbz and Boc protecting groups) that allows for synthesis of a completely protected macrocycle intermediate (e.g., a completely protected CYCLEN) without secondary amines. For example, a tetra-carbomate intermediate is easily purified by column chromatography, removal of Cbz groups using Pd/C-catalyzed hydrogenation provides a di-Boc-protected intermediate, which can be further used for alkylation/modification with the substituents, which are not compatible with hydrogenation reaction conditions. More labile Boc groups can be easily deprotected under acidic conditions together with other acid-labile protecting groups (PG) on the pendant groups.

Coordination chemistry of Fe(II) and Ni(II) are dependent on the coordination number. The compounds of the present invention have donor groups which can be part of the macrocyclic core, also referred to as macrocycle donors, and donor groups part of the substituents on the macrocyclic core, also referred to as pendant donors. For example, when Fe(II) is complexed to a compound of the present invention, 5 to 8 donors (macrocycle donors or pendant donors) are complexed to the Fe(II) center, or when Ni(II) is complexed to a compound of the present invention 4 to 7 donors (macrocycle donors or pendant donors) are complexed to the Ni(II) center. There macrocyclic compound can have various combinations of macrocycle donors and pendant donors. For example, the macrocyclic core can have from 2 to 5 donors and from 2 to 6 pendant donors. In various examples, there are 2 macrocycle donors and 3 pendant donors, 2 macrocycle donors and 4 pendant donors, 2 macrocycle donors and 5 pendant donors, 2 macrocycle donors and 6 pendant donors, 3 macrocycle donors and 2 pendant donors, 3 macrocycle donors and 3 pendant donors, 3 macrocycle donors and 4 pendant donors, 3 macrocycle donors and 5 pendant donors, 3 macrocycle donors and 6 pendant donors, 4 macrocycle donors and 2 pendant donors, 4 macrocycle donors and 3 pendant donors, 4 macrocycle donors and 4 pendant donors, 5 macrocycle donors and 2 pendant donors, or 5 macrocycle donors and 3 pendant donors.

Examples of suitable macrocycle compounds include:

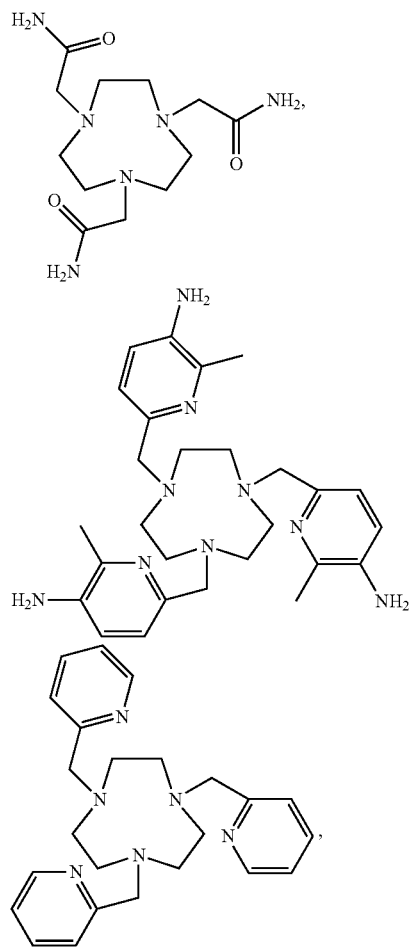

-continued

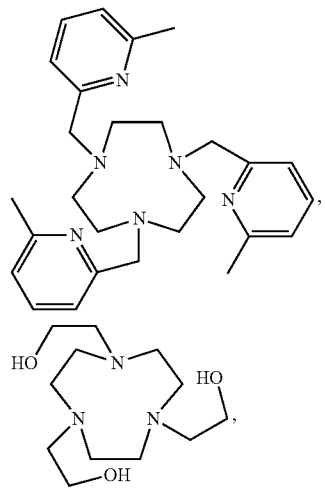

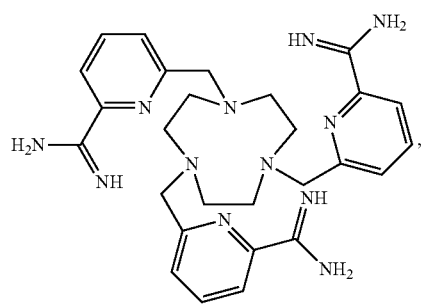

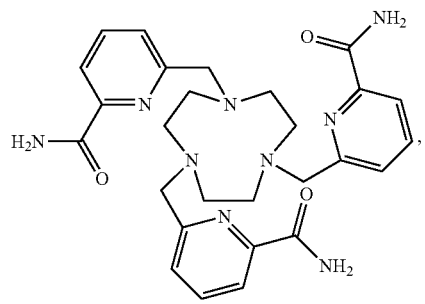

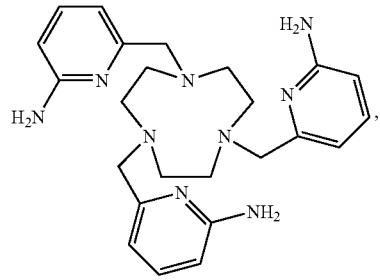

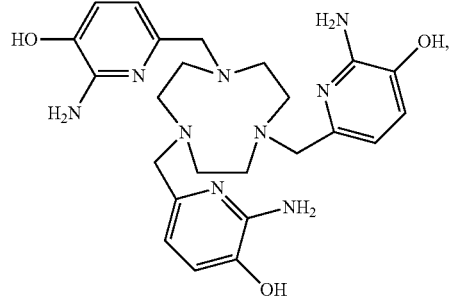

17
-continued
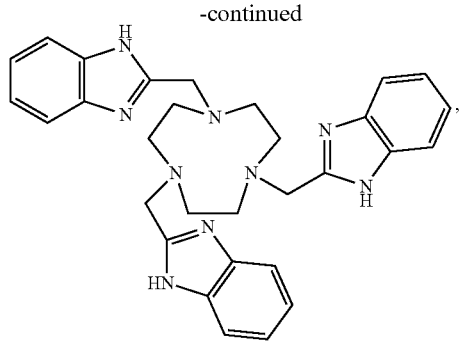
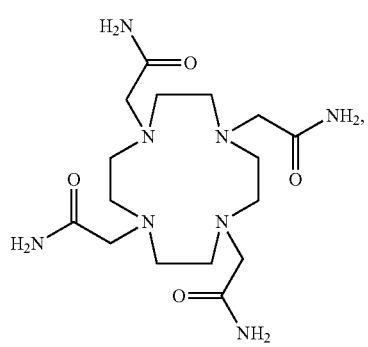
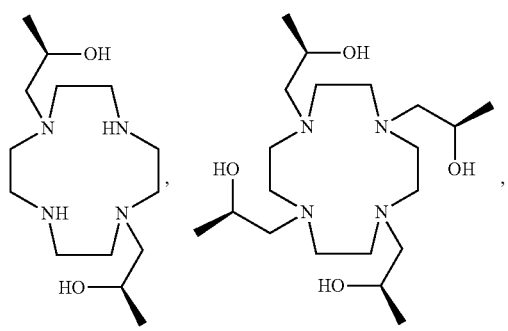
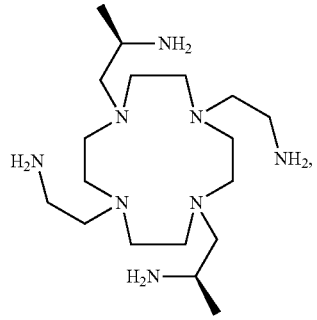
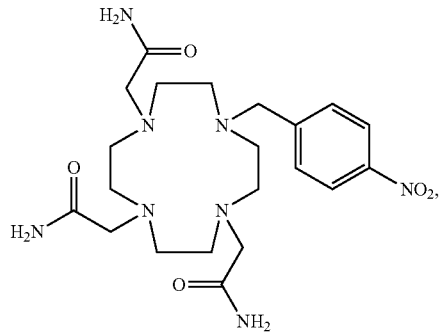
18
-continued
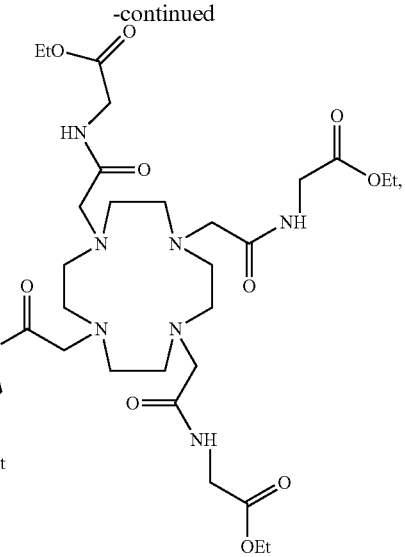
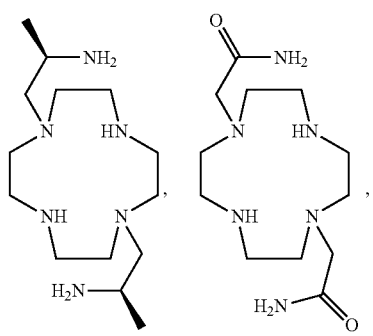
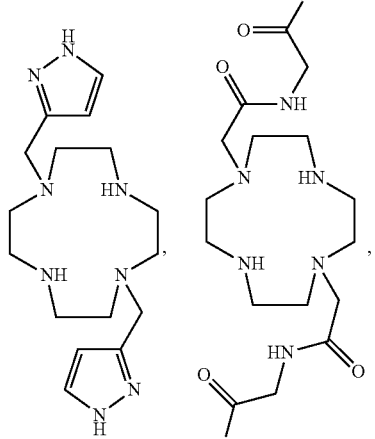
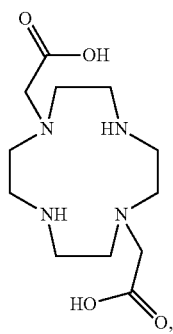

-continued

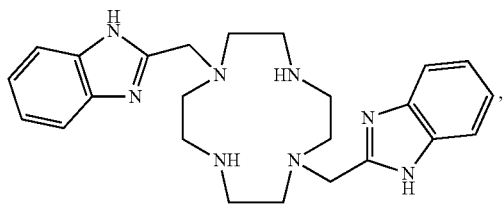

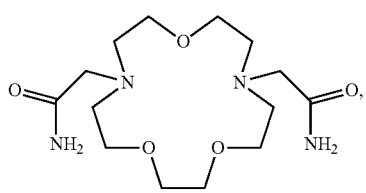

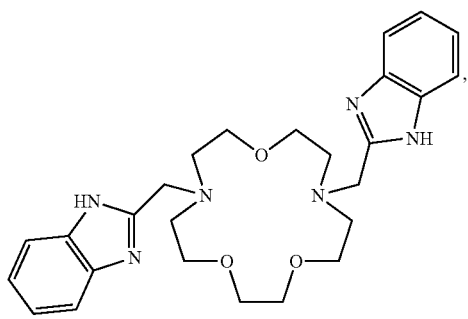

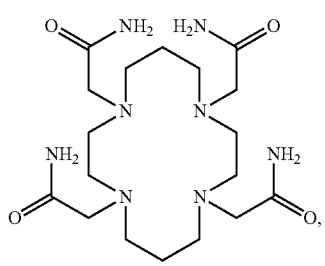

-continued

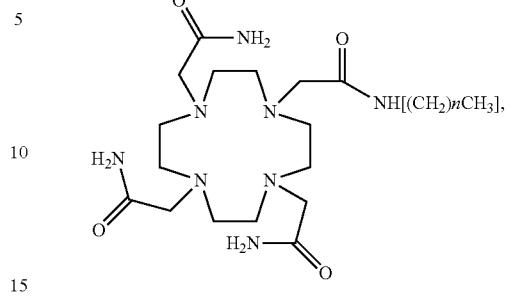

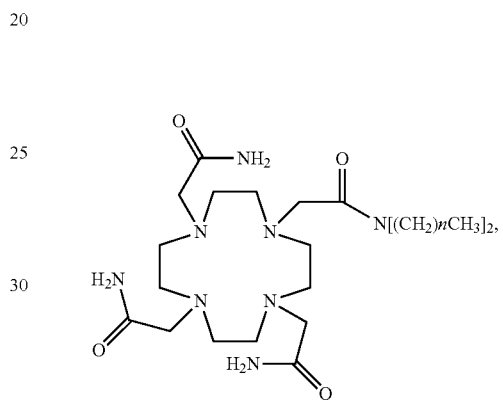

where n is from 6 to 17 and a Fe(II) or Ni(II) cation is complexed to the macrocyclic compound. In an embodiment, a Fe(II) or Ni(II) cation is not complexed to the compound.

It is desirable the macrocycle be rigid. The rigidity of the metal ion complex can be influenced by both the pendent group and substituents in the macrocyclic ring backbone (macrocyclic core). For example, the benzimidazole and methylpyridine or aminopyridine pendent groups give rigid structures with the 1,4,7-triazacyclononane framework bound to Fe(II). Alternately, the chiral hydroxypropyl groups also promote formation of a more rigid Ni(II) or Fe(II) complex when combined with either 1,4,7-triazacyclononane or 1,4,7,10-tetraazacyclododecane. In addition, the incorporation of a substituent in the macrocycle backbone, such as a methyl group, facilitates the arrest of the macrocycle fluxionality in a metal ion complex.

In an embodiment, the compounds of the present invention can have more than one macrocyclic core tethered together via a polymer, dendrimer, protein, or peptide. For tumor uptake and retention, the size of the molecule containing the contrast agent is important. In addition, given that the magnitude of the CEST signal increases proportionally with the number of exchangeable protons, the use of multiple tethered macrocyclic complexes should increase contrast. For example, such a compound can have the following structure:

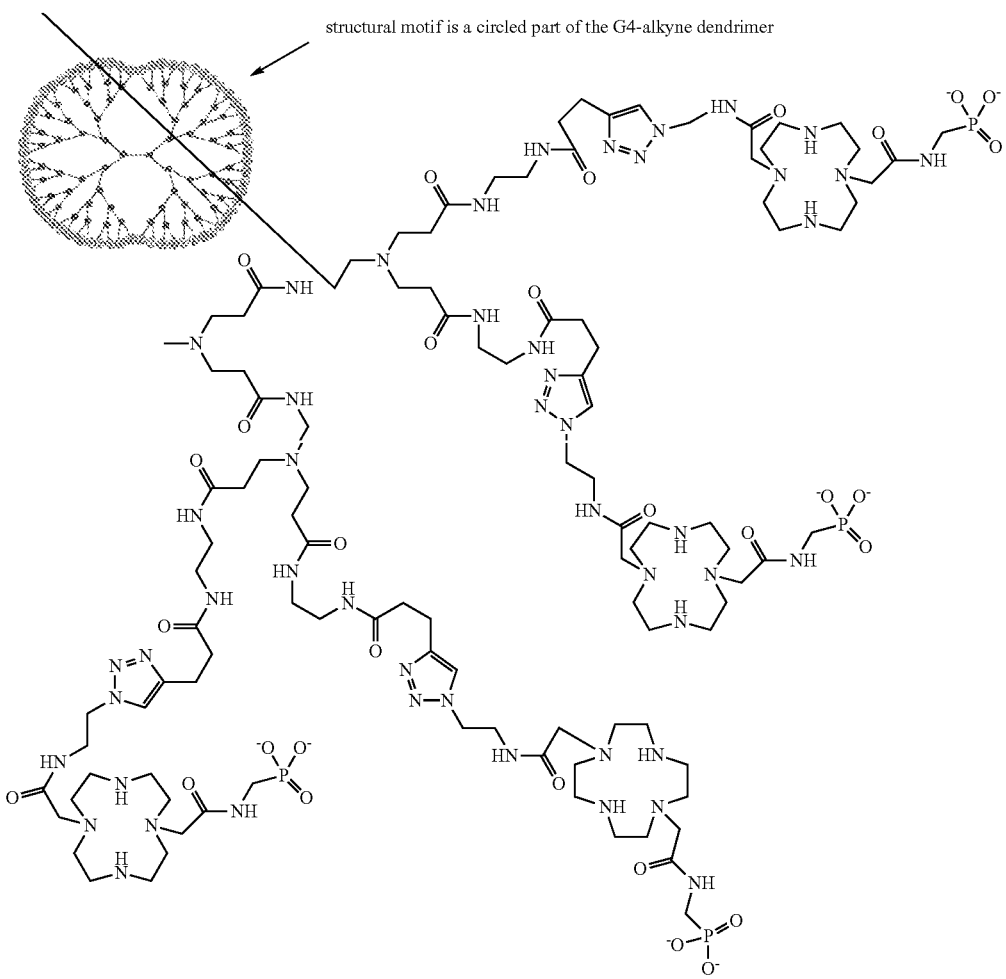

Optionally, the compound is complexed to an Fe(II) or Ni(II) cation.

In various embodiments, the compounds of the invention are a salt, a partial salt, a hydrate, a polymorph, a stereoisomer or a mixture thereof. The compounds can have stereoisomers. For example, the compound can be present as a racemic mixture, a single enantiomer, a single diastereomer, mixture of enantiomers, or mixture of diastereomers. In certain embodiments, after complexation of the metal the compounds are present as mixtures of diastereomers and/or conformers which can be determined by NMR. The diastereomers arise from the conformation of the macrocyclic core and the directionality of the substituents on the macrocyclic core.

The macrocycle compounds of the invention have exchangeable protons. For example, the compounds have from 1 to 12 exchangeable protons. In various examples, the compounds have 1, 2, 3, 4, 5, 6, 7, 8, 9, 10, 11, or 12 exchangeable protons. In the case of compounds with tethered macrocycle compounds, the compounds can have from 1 to 12 exchangeable protons per Fe(II) complex or Ni(II) complex. This may provide hundreds to thousands of exchangeable protons if there are 10-100 Fe(II) complexes or Ni(II) complexes incorporated into, for example, a liposome or polymer. As used herein, "exchangeable proton(s)" are generally those on N, O, and S atoms (e.g., —OH, —NH, —SH) and in some cases can be —CH if the hydrogen atom is acidic enough (i.e., has a pKa<15). The $pK_a$ of the exchangeable proton is from 6 to 15 and all $pK_a$ ranges there between. Rate constants for exchangeable protons are generally in the range of from 100 to 10,000 $s^{-1}$. The optimal rate constant ($k_{CE}$) is as large as possible as long as the $^1H$ NMR spectrum is in slow to intermediate exchange (i.e., the rate constant (units $s^{-1}$ or Hz) may not be larger than the separation between the bulk water protons and the exchangeable protons ($\Delta\omega$ in Hz)) as in Eq. 1.

$$\Delta\omega \geq k_{CE} \quad \text{Eq. 1}$$

The compounds of the present invention are thermodynamically stable and/or kinetically inert towards dissociation. In an embodiment, the compounds are thermodynamically stable and kinetically inert towards dissociation In an embodiment, the kinetic inertness of the compounds of the present invention can be described using a rate constant for dissociation. In an embodiment, the macrocyclic donors and pendant donors do not dissociate appreciably from the metal center for up to 12 hours at neutral pH in the presence of 1) 25 mM carbonate, 0.40 mM phosphate, 100 mM NaCl, pH 7.5; 2) pH 4, 100 mM NaCl; 3) with 10-fold excess $ZnCl_2$, 100 mM NaCl, pH 7.5. Thermodynamic stability is also high. The logarithm of the equilibrium constant for binding of the macrocycle to the metal ion (log K) is between 7 and 20 in the presence of 100 mM NaCl.

In an embodiment, Fe(II) and Ni(II) are high spin (i.e., paramagnetic). For paraCEST, a paramagnetic spin state is needed. In order to keep Fe(II) in the high spin state, the ligand (or crystal) field splitting must not be too large. If the crystal field splitting is larger than the pairing energy, a diamagnetic low spin state will result.

The paramagnetic induced proton shifts of the Fe(II) and Ni(II) complexes are dependent on a number of factors. Paramagnetic induced proton shifts (PIPS) arise from contact (through-bond) and pseudocontact (through-space, dipolar) contributions. These contributions are in addition to inductive diamagnetic effects which are inherent within the compounds of the present invention but are relatively small (Eq. 2):

$$\delta_{PIPS} = \delta_{cont} + \delta_{pseudo} + \delta_{dia} \qquad \text{Eq. 2}$$

Transition metal ions with moderately large anisotropic magnetic moments have strong dipolar contributions to PIPS. However, potentially larger contact shifts are anticipated with transition metal ions due to the larger degree of covalency in their metal-ligand bonds. In an example, the large chemical shift difference of 50 to 70 ppm between the two amide protons in the Fe(II) complexes or 70 ppm for the Ni(II) complexes that contain amide pendent groups of the compounds disclosed is mediated by the multiple-bond character of the N—C bond through contact shift contributions as determined by theoretical calculations. Dipolar shift contributions are a result of through-space interactions between the unpaired electrons and the nucleus. They are dependent on the distance of the proton from the metal ion center, the magnitude of the magnetic anisotropy tensor and the angle of the proton with respect to the principal axis of the magnetic susceptibility tensor. Large dipolar shifts are generally observed for protons that are 2-3 bonds away from the metal ion center. Contact shifts are proportional to the unpaired spin density at the proton. Spin density arises from a combination of direct delocalization and spin polarization. Contact shifts are dependent on the hyperfine coupling constant and the spin expectation value as transmitted through bonds. Contact shifts may have an impact on PIPS over relatively long distances, especially in conjugated systems. In an embodiment, primarily contact shifts occur over 3 to 5 bonds from the Fe(II) or Ni(II) center. In an example, the dipolar and contact shift contributions of paramagnetic Fe(II) complexes make it feasible to use donor groups with (proximal) exchangeable protons such as the NH of amides as well as more remotely located groups connected through a ligand pi system such as amino-pyridines.

In an embodiment, the compounds of the invention are stable towards chemical reaction in an oxidative environment (i.e., in the presence of biologically relevant concentrations of peroxide or oxygen). In an embodiment, the stability in an oxidative environment can be related to the reduction potential of the complex. In an embodiment, the compounds of the present invention have a reduction potential greater than 600 mV vs. NHE (Normal Hydrogen Electrode) as shown in Table 1. Generally, the compounds of the invention have a reduction potential above 800 mV vs. NHE.

For use in the invention, the compounds described herein can be administered as pharmaceutical preparations. Thus, they can be provided in a variety of solutions of various compositions, and can be combined with one or more standard pharmaceutically acceptable carriers. Some examples of pharmaceutically acceptable carriers can be found in: *Remington: The Science and Practice of Pharmacy* (2005) 21st Edition, Philadelphia, Pa. Lippincott Williams & Wilkins.

Various methods known to those skilled in the art may be used to introduce the compositions of the invention to an individual. These methods include but are not limited to intravenous, intramuscular, intracranial, intrathecal, intradermal, subcutaneous, and oral routes. In one embodiment, the composition is administered intravenously. The composition can be provided as a liquid, a solution, or a solid, and may be provided in combination with any suitable delivery form or vehicle, examples of which include but are not limited to caplets, capsules, tablets, an inhalant or aerosol, etc. The dose of the composition to be used will necessarily be dependent upon the needs of the individual to whom the composition of the invention is to be administered. These factors include but are not necessarily limited to the weight, age, sex, and medical history of the individual.

The necessary solubility of the complexes depends on their effectiveness in producing contrast. For paraCEST contrast agents that have CEST peaks shifted greater than 120 ppm from the proton resonance of bulk water, the complexes need 20 to 100 µM (micromolar) solubility. For paraCEST complexes that have peaks of less than 100 ppm, solubility must be in the low millimolar range. For Fe(II) and Ni(II) complexes used for MRS, complexes should have solubilities of 1-20 mM. Solubility is generally measured in aqueous solution at near neutral pH (6.5 to 7.5) in 100 mM NaCl with 25 mM carbonate and 0.4 mM phosphate.

In an aspect, the present invention provides imaging methods using the macrocyclic compounds. In an embodiment, the invention provides a method to obtain an image of at least a portion of a cell, organ, vasculature, or tissue comprising the steps of: contacting a cell, organ, vasculature or tissue with the compounds of the invention, and imaging at least a portion of the cell, organ, vasculature or tissue to obtain an image of the portion of cell, organ, vasculature or tissue.

In an embodiment, the portion of a cell, organ, or tissue is part of an individual. By "individual" it is meant a human or animal. The at least part of a cell, tissue, or organ can be alive or dead. Likewise, the individual can also be alive or deceased.

In an embodiment, the image of the method can be obtained by a number of imaging techniques. In an embodiment, the imaging technique can be MRI. In an embodiment, the disclosed compounds will act as magnetic resonance imaging (MRI) contrast agents through paramagnetic chemical exchange saturation transfer (paraCEST), and the disclosed methods will utilize the same.

Figure 14:
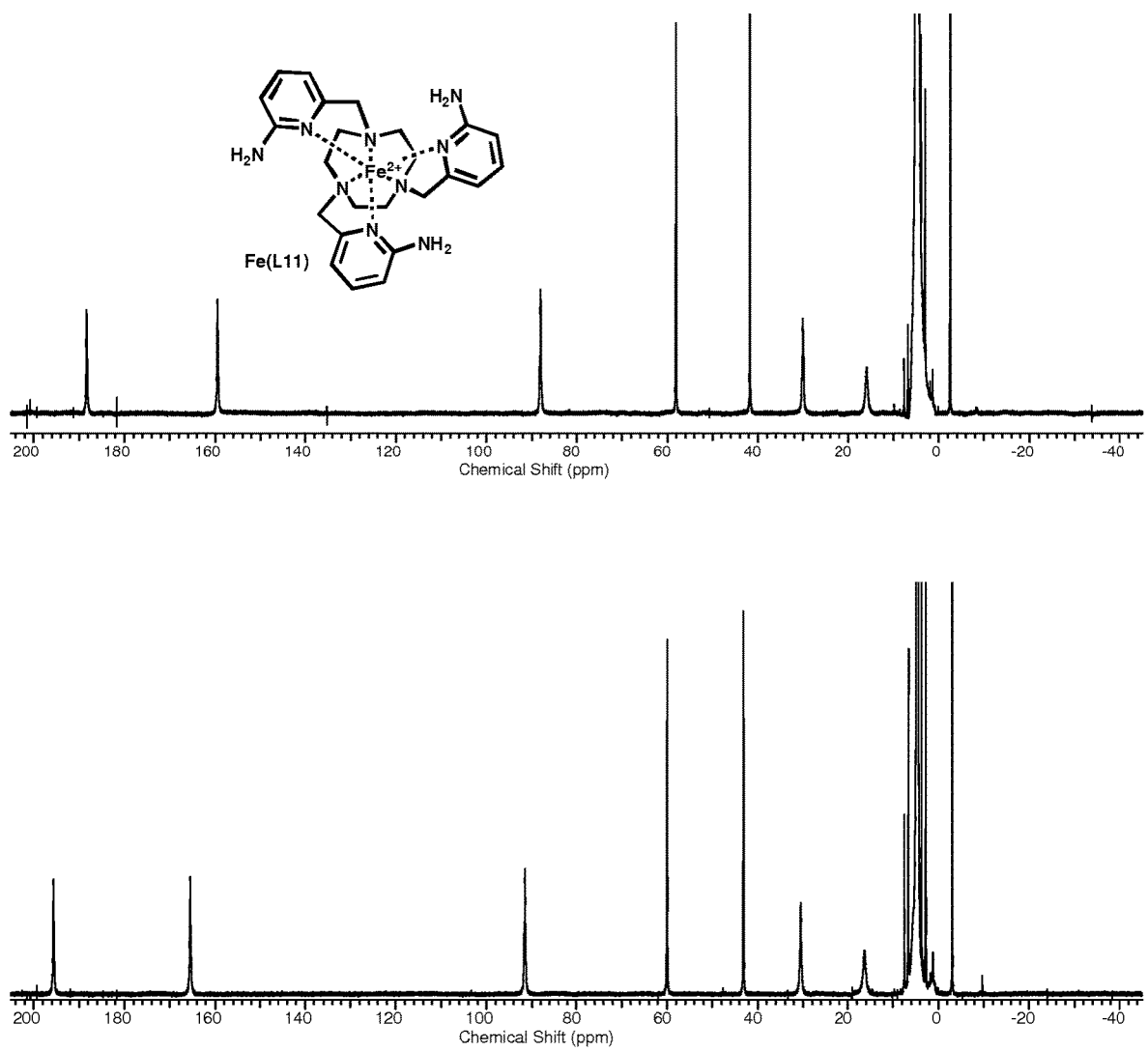
FIG. 14. Representative $^1$H NMR of Fe(L8) in D$_2$O showing the temperature dependence of the non-exchangeable protons from 25° C. (bottom spectrum) to 37° C. (top spectrum).

In an embodiment, the imaging technique can use MRSI (also referred to herein as CSI). MRSI is used to measure the levels of different metabolites in body tissues. The MR signal produces a spectrum of resonances that correspond to different molecular arrangements of the isotope being "excited". In an embodiment, the compounds can be used in Magnetic resonance spectroscopic imaging (MRSI). In an embodiment, the imaging technique can be MRSI. MRSI combines both spectroscopic and imaging methods to produce spatially localized spectra for each voxel from within the sample or patient. The spatial resolution is much lower (limited by the available signal to noise ratio and memory availability for data storage), but the spectra in each voxel contains information about many metabolites. Preliminary experiments involved taking the proton NMR spectrum of the complexes in solutions containing 100 mM NaCl, 25 mM carbonate, 0.4 mM phosphate as a function of temperature (see FIG. 14) on a high field NMR spectrometer (300-500 MHz). The spectra were acquired and averaged for about 10 minutes and a proton NMR spectrum was obtained. Future experiments will involve taking the proton NMR spectrum in blood plasma taken from a laboratory mouse and in vivo on a MRI scanner. The spectrum will be created by using multi-voxel spectroscopic techniques and water suppression.

In an embodiment, the macrocyclic compound of the method can be a Chemical Exchange Saturation Transfer (CEST) agent. CEST exploits the ability of Nuclear magnetic Resonance (NMR) to resolve different signals arising from protons on different molecules. By selectively saturating a particular proton resonance of the compounds of the present disclosure that is in exchange with the surrounding water molecules, the MRI signal from the surrounding bulk water is also attenuated. A requirement for off-resonance saturation is that chemical exchange of the proton between contrast agent and water must be in the intermediate regime where exchange is fast enough to efficiently saturate the bulk water signal but slow enough on the NMR timescale to retain two proton resonances. In other words, there is a chemical shift difference between the exchangeable proton and the bulk water proton resonances. Paramagnetic metal ions (such as iron) shift the proton ($^1$H) resonances of substituents that bind to them. Design of a paraCEST agent involves incorporation of at least one exchangeable proton into the compound. The exchangeable proton should be placed such that its $^1$H resonance is shifted substantially by interaction with the iron. Application of a frequency selective presaturation pulse at the resonance of the exchangeable proton prior to the NMR spectroscopy experiment gives rise to the paraCEST spectrum which maps the water proton intensity as a function of presaturation pulse frequency. In an embodiment, the difference between the bulk water signal and the exchangeable proton is from 40 to 250 ppm, from the proton resonance of bulk water.

It is important to produce exchangeable proton resonances that are sufficiently shifted from bulk water to avoid the endogenous macromolecule magnetization transfer (MT) effect. Obtaining the highly shifted proton resonance (large Δω from bulk water) that would avoid sensitivity loss in vivo due to endogenous MT has been a difficult hurdle to overcome. Shifting the exchangeable proton resonance by >120 ppm away from the bulk water resonance will lead to more sensitive contrast agents that will enable their development for pH and temperature sensing by avoiding MT effects.

The detection sensitivity of CEST agents depends on several factors including the rate constant for proton exchange, the number of exchangeable protons, the concentration of the contrast agent, the value of $T_1$ for water protons in the presence of the agent and the pulse power and duration. Eq. 3 is derived from the assumption that the magnetization of the exchangeable proton is saturated and defines the CEST effect as the net reduction in the water magnetization ($M_z/M_o$).

$$\frac{M_Z}{M_0} = \frac{1}{1 + k_1 T_1}$$
$$k_1 = n[\text{agent}]k_{CE}$$

Eq. 3 where $k_{CE}$ is the single site exchange rate, n is the number of exchangeable protons/molecule, and $T_1$ is the water spin-lattice relaxation time in the presence of the saturating pulse. A large n is accomplished by incorporating symmetry into the macrocyclic compound.

In an embodiment, the macrocyclic compound of the method can be a paraCEST agent. paraCEST is a novel contrast mechanism that is important during in vivo imaging due to the complex biological environment. Studies of these compounds have revealed that, in solution, MRI was able to reliably image agents designed to detect iron(II). The complexes are stable as high spin Fe(II) and Ni(II) under physiologically relevant conditions and contain multiple protons for exchange with bulk water.

In another embodiment, the macrocyclic compound of the method can be a thermometry agent. The compounds disclosed are ideal for development as a temperature dependent MRS agent for an application known as thermometry—temperature sensing in vivo. The change in the chemical shift of the proton resonances of paramagnetic metal ion complexes is proportional to temperature over a narrow temperature range. In another embodiment, the compounds disclosed will be used for temperature dependent chemical shift imaging (thermometry). The proton resonances must be relatively sharp for the experiment to have a good signal to noise ratio; broad peaks are hard to image with high signal to noise. It is beneficial to irradiate the proton resonances with greatest number of equivalent protons (i.e., $CH_3$) and have them be highly shifted for imaging in thermometry. The best thermometry agents have large temperature coefficients (CT, chemical shift change per degree=Δδ/° C.) and narrow linewidths (FWHM) to distinguish small temperature changes of 0.05° C. to 0.5° C. The most useful parameter is CT/FWHM which takes into account both shift with temperature and linewidth. In an embodiment, the CT/FWHM of the compounds of the invention is 0.3 to 5.0. In addition, the protons used for thermometry should be shifted at least 30 ppm from bulk water.

In this application, the highly shifted proton resonances of the Fe(II) complexes are monitoring for magnetic resonance imaging. Some of the Fe(II) complexes are suitable as dual paraCEST MR imaging contrast agents and chemical shift imaging agents.

In yet another embodiment, the macrocyclic compound of the method can be a pH mapping agent. The compounds of the invention can be used as pH probes in at least a portion of a cell. In an embodiment, at least a portion of the cell can be part of a brain. In an embodiment, the at least portion of a cell can be a tumor cell. In addition to being temperature dependent, the non-exchangeable proton resonances of paramagnetic complexes may be pH dependent. Compounds that have proton resonances that vary with both pH and temperature have been developed for simultaneous pH and temperature sensing. In another embodiment, the compounds are dual paraCEST/thermometry agents.

The following examples are presented to illustrate the present invention. They are not intended to be limiting in any manner.

Example 1

Example of Fe(II) and Ni(II) macrocyclic compounds as CEST and MRI paraCEST agents.

Figure 2:
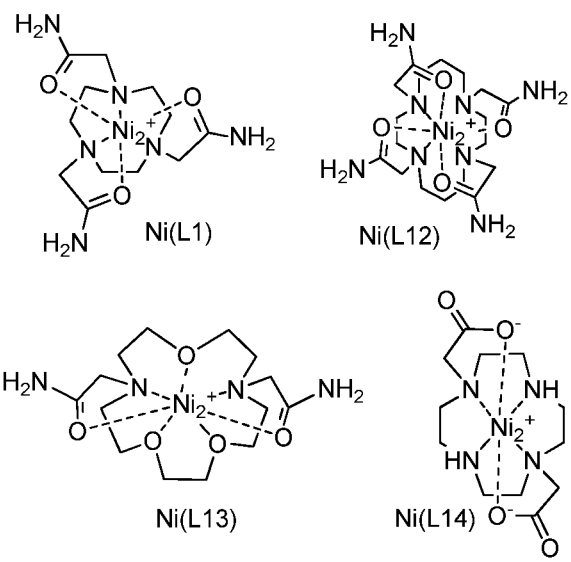
FIG. 2. Examples of Ni(II) macrocyclic compounds of the present disclosure featuring exchangeable NH groups.
Figure 3:
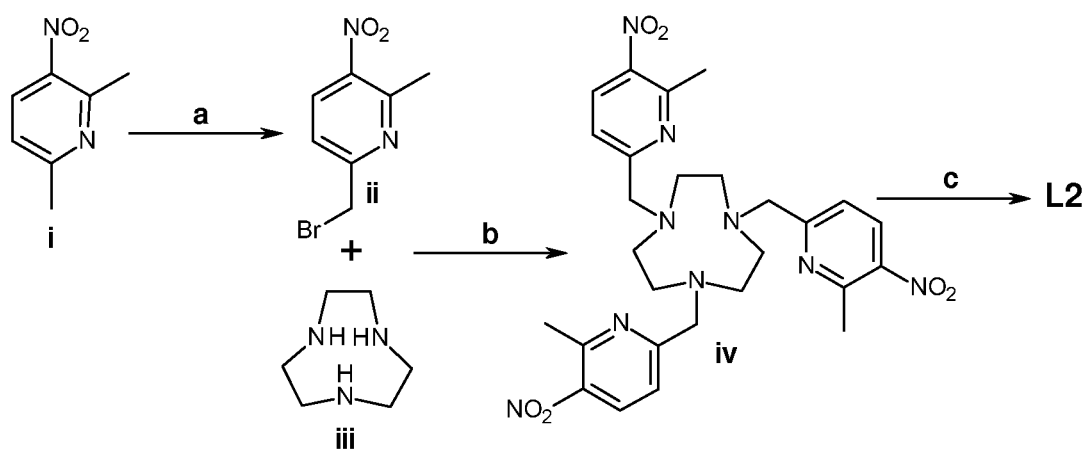
FIG. 3. Example of synthesis of L2. Reagents and conditions: (a) NBS (N-bromosuccinimide), AIBN (azobisisobutyronitrile), carbon tetrachloride, 50° C. to reflux, Ar, 8 hours; (b) TEA, acetonitrile, 50° C., 24 hours; (c) hydrogen, 10% Pd/C, methanol, 8 hours.

Fe(II) paraCEST agents were developed by preparing ligands that stabilize Fe(II) and Ni(II), contain multiple exchangeable protons to enhance the CEST effect and form six or eight coordinate complexes to protect the Fe(II) from binding additional ligands that might complicate the CEST signal. The sexadentate ligands contained the macrocycle, 1,4,7-triazacyclononane, with three pendent groups while the octadentate ligands contained 1,4,7,10-tetraazacyclododecane and four pendent groups (FIG. 1 and FIG. 2). Pyridine pendent groups stabilize Fe(II) relative to Fe(III) (L2, L3), and amide pendent groups are stabilizing of Fe(II) (L1). For example, the pyridine groups in Fe(L3) lead to a high reduction potential of +930 mV vs. NHE. Amide groups contain exchangeable protons and have been commonly used as a basis for Ln(III) paraCEST agents. In contrast, amino pyridine pendent groups and the benzimidazole groups have exchangeable protons that are one bond further away from the Fe-coordinated nitrogen of the pyridine ring. Exchangeable protons close to the Fe(II) center as well as more remotely located protons appended to a ligand pi-system have been studied in this work in order to capitalize on both the dipolar and contact shift contributions of paramagnetic Fe(II). The strategy of using exchangeable protons that are remote from the metal ion center was explored in order to capitalize on both the dipolar and contact shift contributions of paramagnetic Fe(II). Fe(II) complexes were prepared in acetonitrile or in aqueous solution by simple addition of the free base form of the ligands to $Fe(CF_3SO_3)_2$. The formation constants as determined by pH potentiometric titrations were log K=13.5, 7.5, 9.3 for Fe(L1), Fe(L4) and Fe(L6), respectively, in 100 mM NaCl (Table 4), demonstrating strong binding of the macrocycles to Fe(II) (Table 4). In addition, some of the Fe(II) complexes are inert towards dissociation at neutral pH, acidic pH or in the presence of metal cations such as Zn(II) or Cu(II). In particular Fe(L4) showed no dissociation after 12 hours incubation at 37° C., at pH 4 or at neutral pH with five equivalents of $CuCl_2$ or $ZnCl_2$. Other macrocycles of notable kinetic inertness toward dissociation under these conditions is Fe(L3). Fe(L4) and Fe(L3) are also remarkably inert towards hydroxylation of benzoate or redox cycling as shown by ascorbate consumption (Table 4).

Amide groups such as those in L1 contain exchangeable NH protons that are located three bonds away from the metal ion center and can be successfully used for Ln(III) paraCEST agents. In contrast, the aminopyridine pendent groups in L2 or benzimidazole groups in L5 have exchangeable protons attached to a pi-system that are four bonds removed from the Fe(II) and have not been previously used for paraCEST agents.

Figure 4:
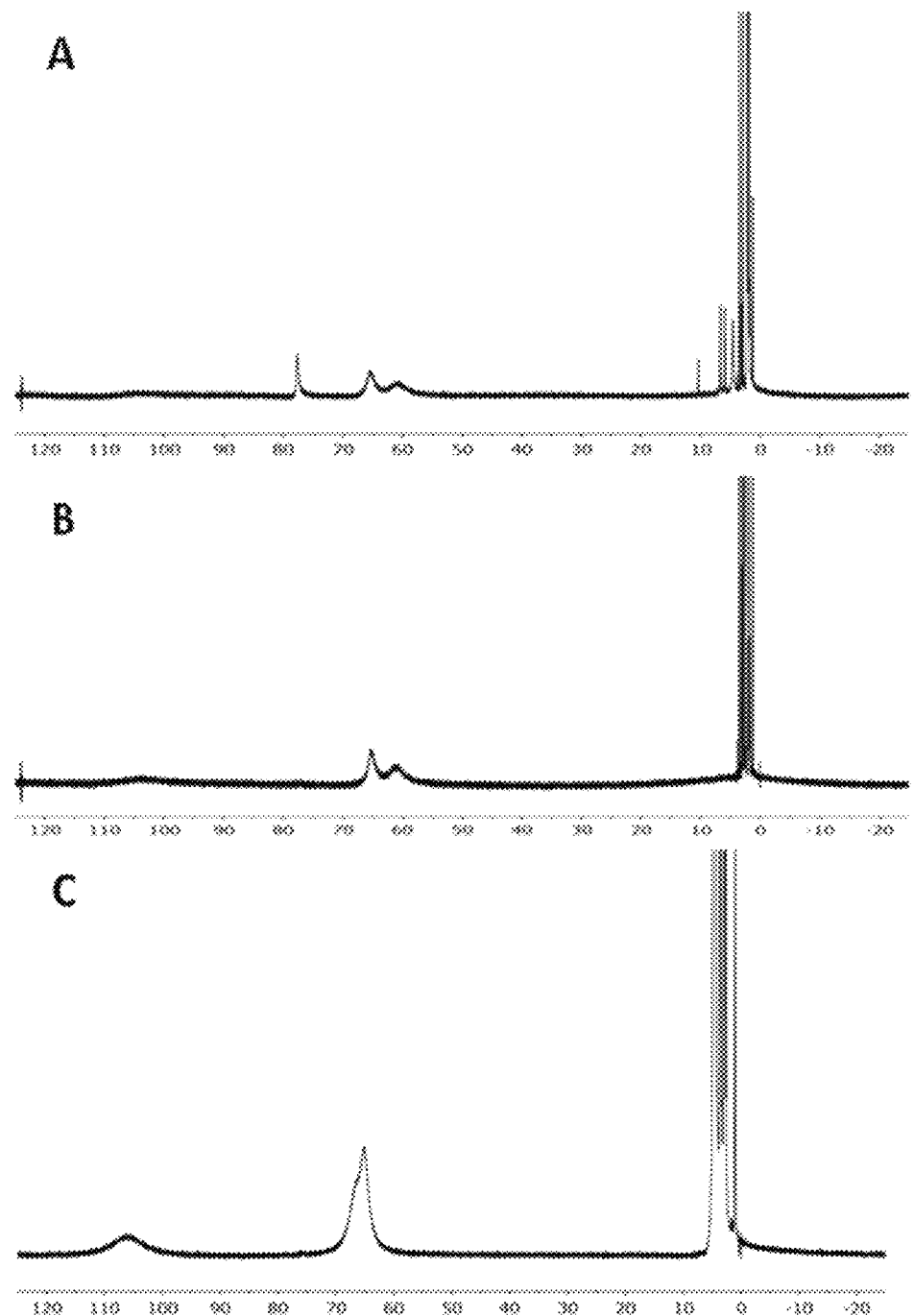
FIG. 4. Representative $^1$H NMR of Fe (L1) in d$_3$-acetonitrile showing amide protons at 75 ppm that give rise to the CEST peak and disappearance of amide protons at 75 ppm upon addition of D$_2$O. 400 MHz $^1$H NMR at 25° C. of Fe(L1) in (A) CD$_3$CN; (B) upon addition of 30 μL D$_2$O; (C) D$_2$O. The proton resonance close to 80 ppm in A disappears when D$_2$O is added, indicating location of the exchangeable amide protons of L1.
Figure 5:
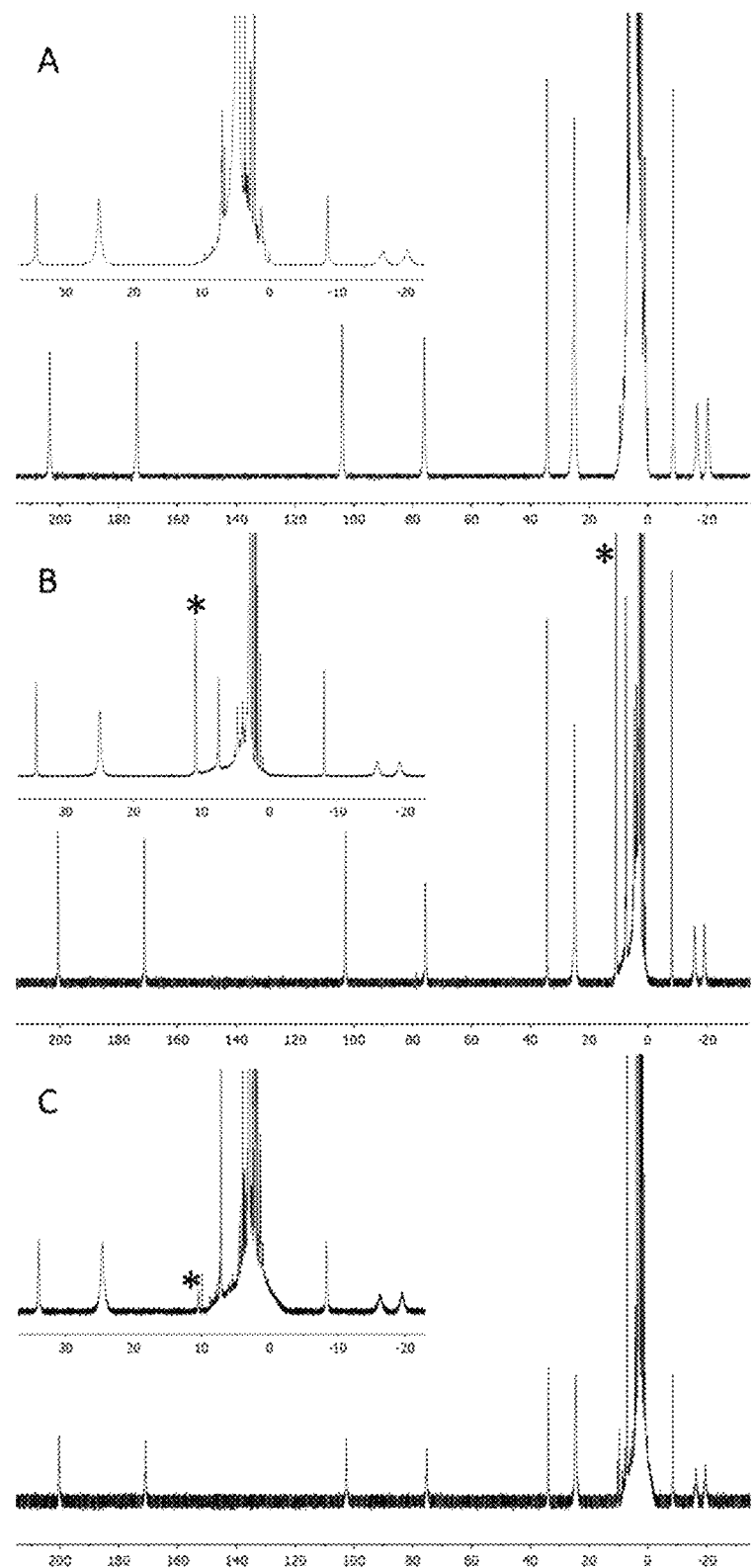
FIG. 5. Representative 500 MHz $^1$H NMR spectra at 25° C., 2 seconds, of the Fe(L2) solutions in: (A) D$_2$O; (B) CD$_3$CN; (C) CD$_3$CN containing 5% D$_2$O. Asterisks indicate peaks corresponding to exchangeable amino protons.

Fe(II) complexes of L1 and L2 are high spin in aqueous solution and resistant to oxidation to Fe(III). Effective magnetic moments are characteristic of high spin Fe(II) at 5.1 BM and 5.8 BM for Fe(L1) and Fe(L2), These were measured in 100 mM NaCl in $D_2O$, pH 7.4, and $D_2O$ at pH 7.0, respectively. The $^1$H NMR spectra of the two complexes show highly shifted proton resonances (FIGS. 4-5). There are nine non-exchangeable proton resonances for Fe(L2) consistent with trigonal prismatic geometry as observed previously for Fe(L3) and three sets of four chemically inequivalent proton resonances in the macrocycle backbone. Thus the Fe(L2) complex, with its narrow proton resonances, is suitable for MRSI. The three broad non-exchangeable protons in the spectrum of Fe(L1) shows that there is a dynamic process on the NMR time scale that averages the protons in the macrocyclic backbone, giving rise to two broad peaks instead of four and one broad peak instead of two for the methylene protons in the pendent group. This shows that Fe(L1) is not suitable for MRSI. The exchangeable amide and amine protons were identified by comparison of the $^1$H NMR spectra of the complexes in $H_2O$ and $d_3$-acetonitrile. For Fe(L1), the amide protons are highly shifted downfield, appearing at 77 ppm. The amine protons of Fe(L2) are only slightly shifted and are observed at 11 ppm. The $^1$H NMR spectra of the complexes did not change over several days, consistent with the persistence of the Fe(II) oxidation state in neutral aqueous solution in the presence of atmospheric oxygen.

Figure 21:
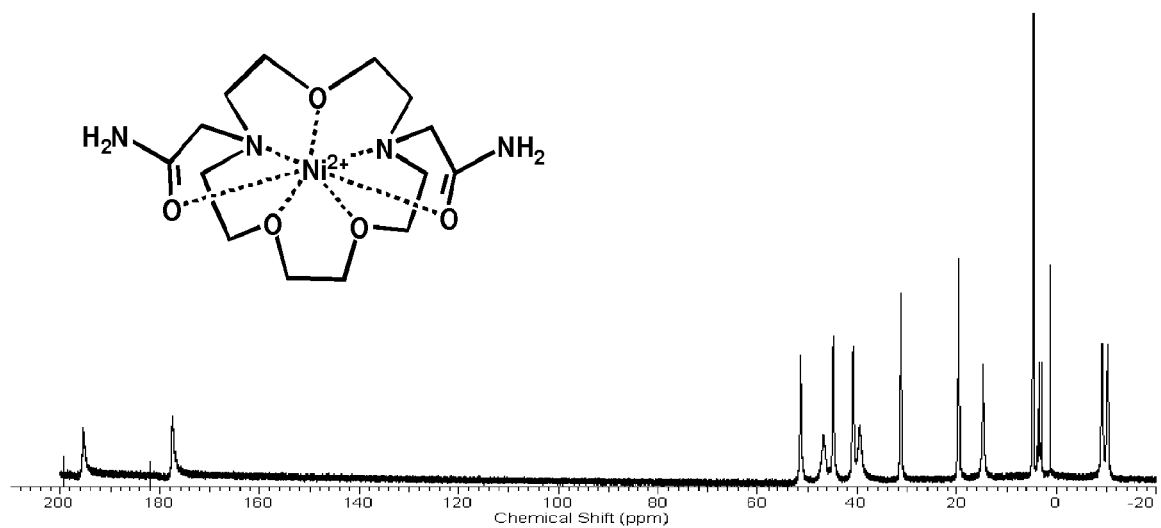
FIG. 21. Representative $^1$H NMR spectrum of a Ni(L13) complex in $D_2O$.

Ni(II) complexes were prepared from macrocyclic ligands that form five, six, or seven coordinate complexes (FIG. 2). The complexes were prepared by adding $Ni(CF_3SO_3)_2$ to the ligand in acetonitrile. The six coordinate complexes, Ni(L1), Ni(L12) were inert towards dissociation in solution at both neutral and acidic pH over a period of at least 24 hours. Ni(L13) shows a highly shifted proton NMR spectrum with narrow proton resonances (FIG. 21).

Figure 7:
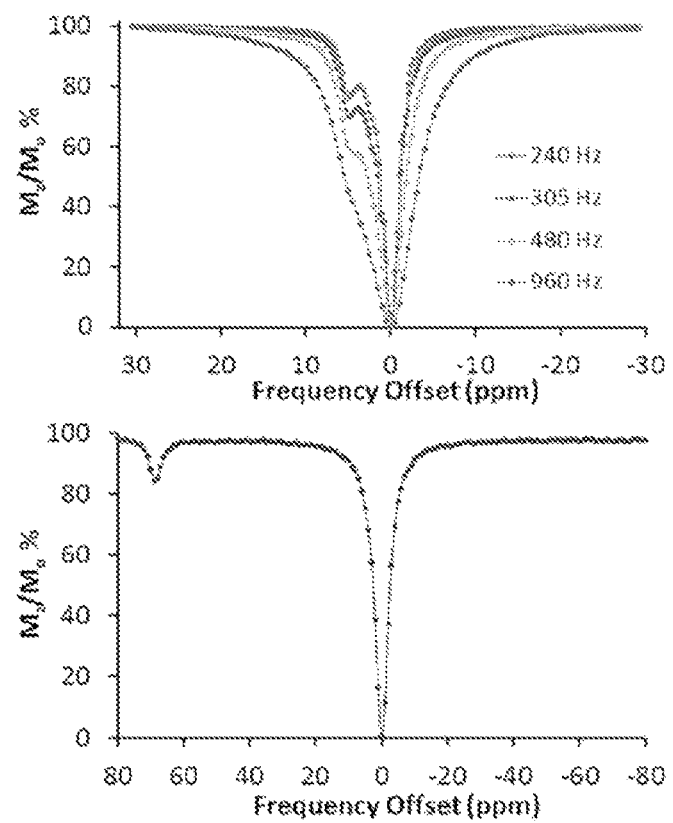
FIG. 7. Representative CEST spectra on a 400 MHz spectrometer of 4.3 mM Fe(L2) at varying B$_1$(top) and 8 mM Fe(L1) (bottom) with B$_1$=960 Hz for Fe(L1) at pH 7.0.
Figure 8:
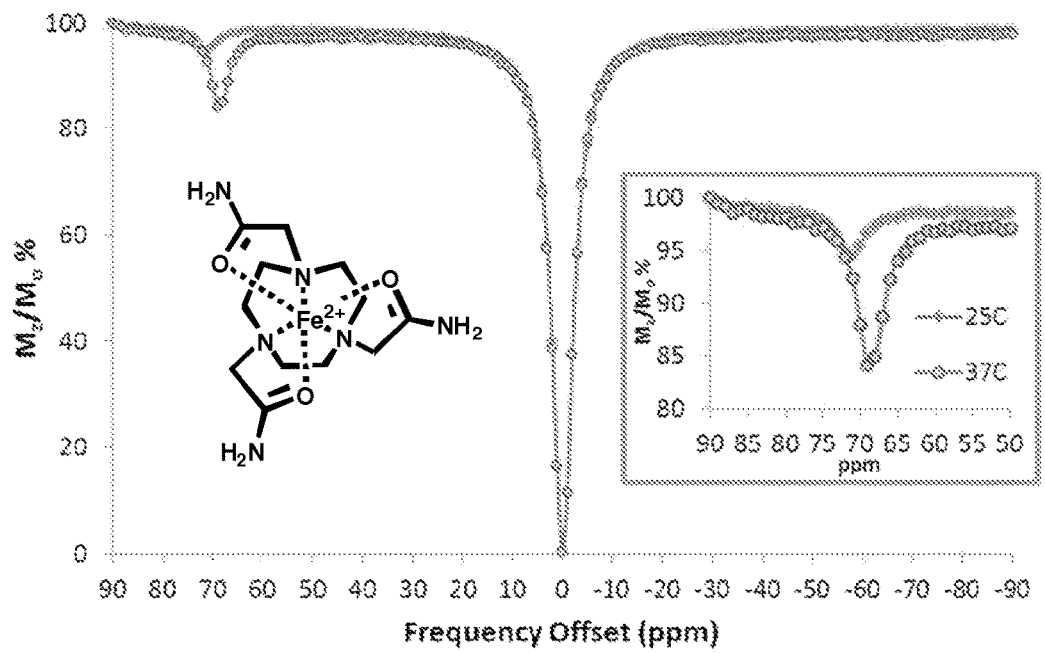
FIG. 8. Representative CEST spectra recorded at 400 MHz of 8 mM Fe(L1), 20 mM HEPES pH 6.85, 100 mM NaCl, B$_1$=960 Hz at 25° C. and 37° C. Inset shows the difference in CEST effect more clearly, in which maximum CEST is observed at 71 ppm at 25° C. and 69 ppm at 37° C., with the larger CEST peak observed at higher temperature.
Figure 9:
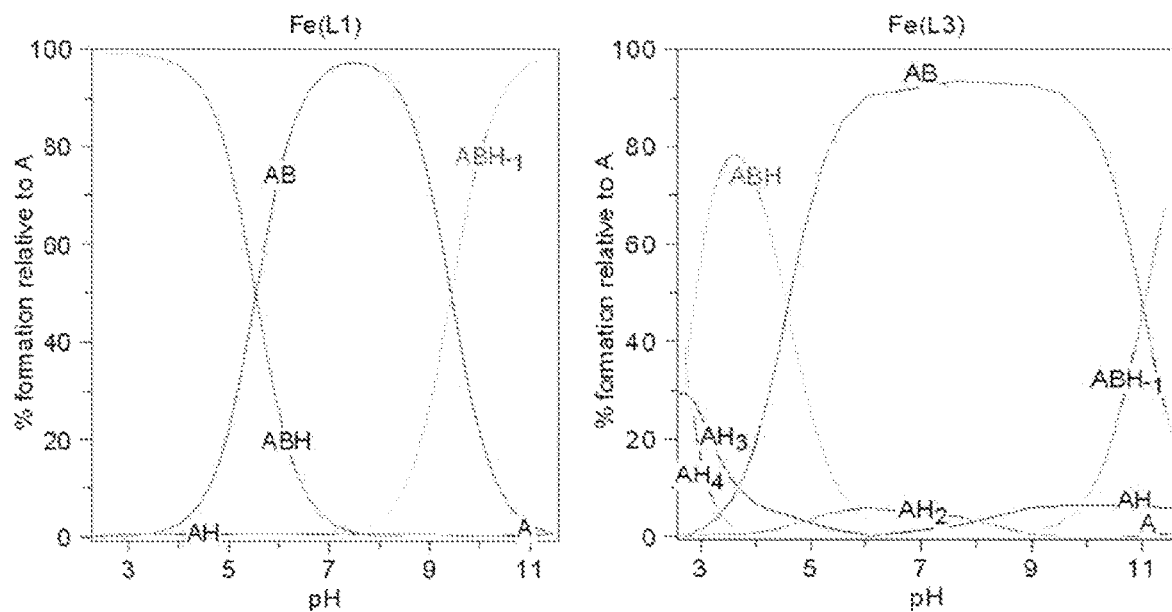
FIG. 9. Representative speciation diagrams showing Fe(II) complexes present in solution as a function of pH for a given concentration of ligand and metal ion. Here A represents the free or neutral macrocyclic ligand, AH$_2$ is the ligand protonated twice, ABH is the Fe(II) complex bound to the ligand with one additional proton, AB is the Fe(II) complex with the neutral ligand, ABH$_{-1}$ is the Fe(II) complex of the ligand with one proton lost from the complex. This data is derived from a fit of data in FIG. 10.
Figure 10:
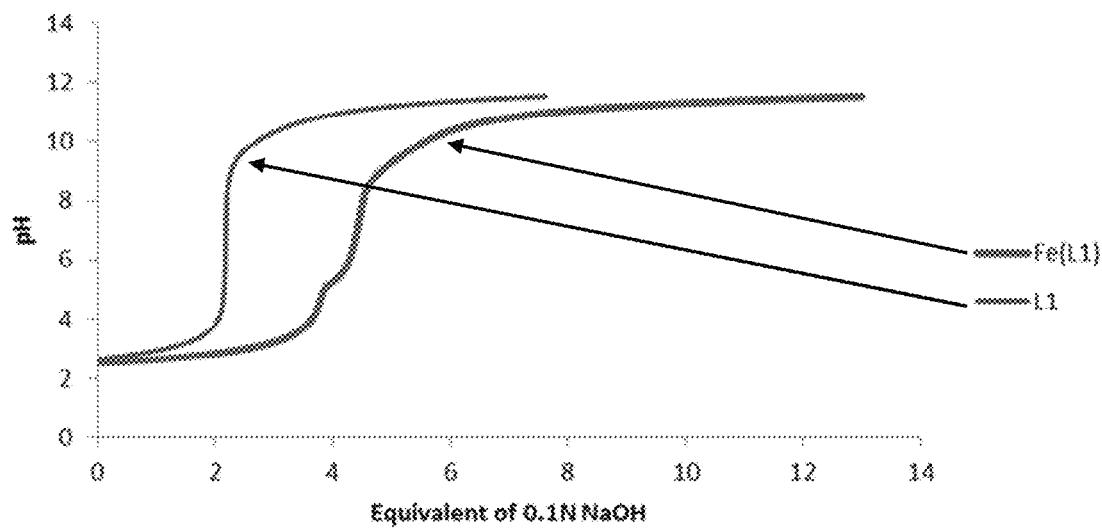
FIG. 10. Representative pH-potentiometric titrations for Fe(L1) and Fe(L3) in 100 mM NaCl at 25° C.
Figure 10:
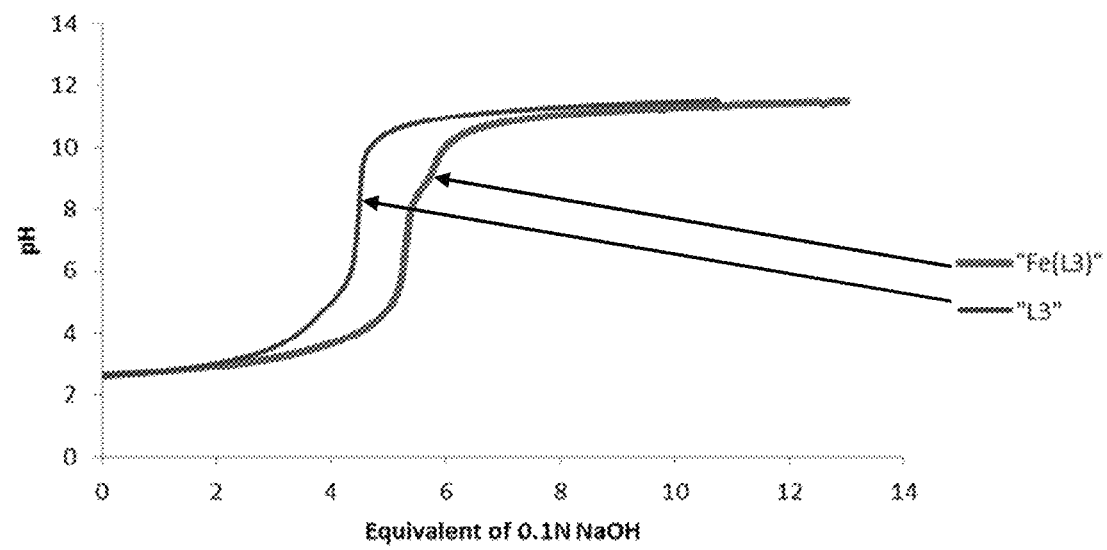
Figure 11:
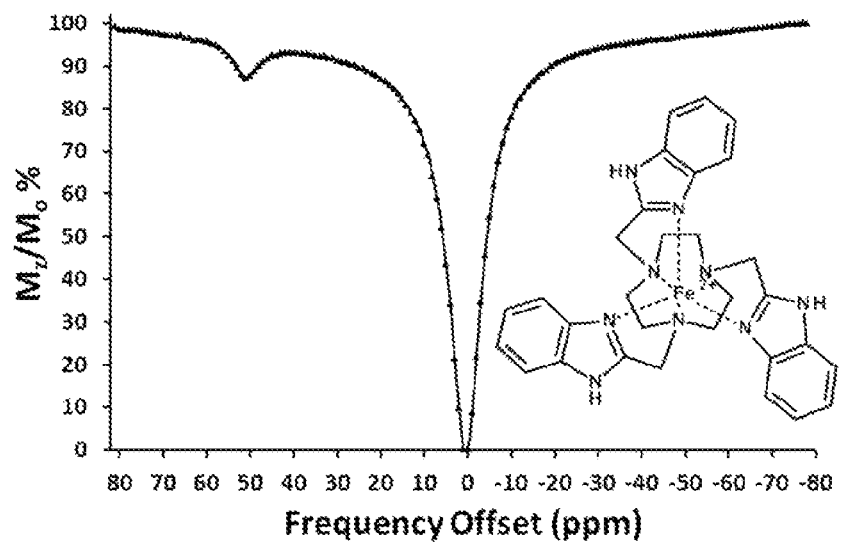
FIG. 11. Example of CEST spectrum of 3 mM Fe(L5) at pH 6.3, collected at 25° C. with B$_1$=980 Hz, 400 MHz spectrometer.

CEST spectra, plotted as the percent reduction of the water proton resonance as a function of the presaturation frequency are shown in FIG. 7 for Fe(L1) and Fe(L2) at near neutral pH. Fe(L1) gives a CEST peak at 69 ppm, arising from the amide protons. Fe(L2) gives a CEST shoulder at 6 ppm, attributed to exchange of the amine protons. CEST spectra as a function of presaturation pulse power are given for Fe(L2) to better show definition of the shoulder in the CEST spectrum. Notably, the CEST effect for Fe(L1) is larger at 37° C. than at 25° C. (FIG. 8).

Figure 19:
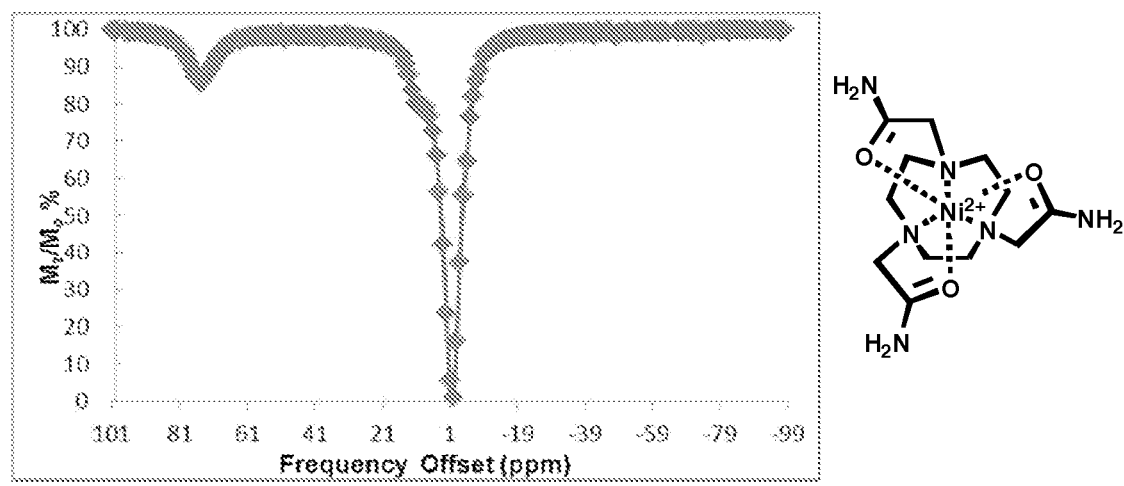
FIG. 19. Representative CEST spectrum recorded at 500 MHz of 10 mM Ni(L1) complex, 100 mM NaCl and 20 mM HEPES at pH 7.3 at 37° C. With $B_1$=1000 Hz, 2 seconds.
Figure 20:
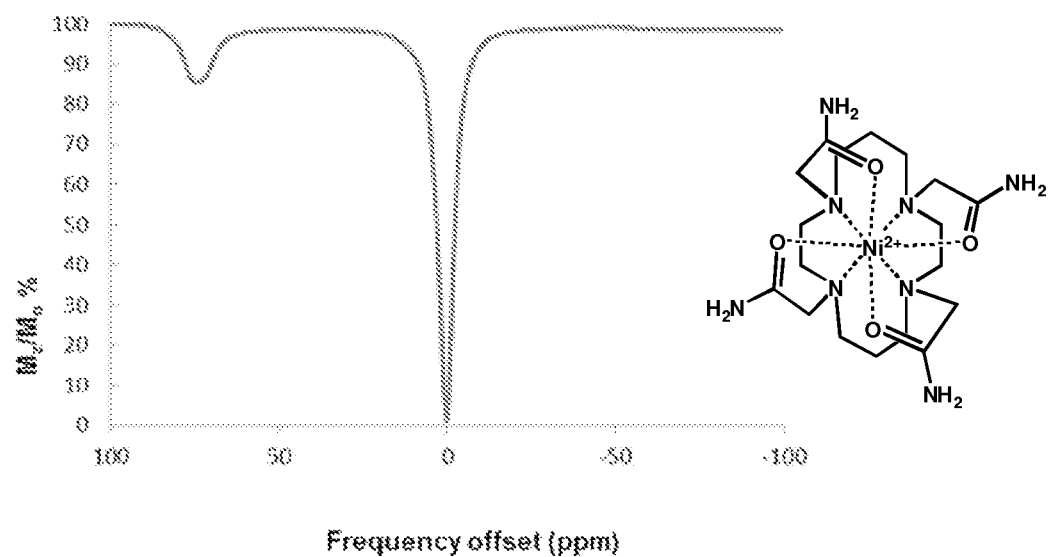
FIG. 20. Representative CEST spectrum recorded at 500 MHz of 10 mM Ni(L12) complex, 100 mM NaCl and 20 mM HEPES at pH 7.5 at 37° C. With $B_1$=1000 Hz, 2 seconds.
Figure 22:
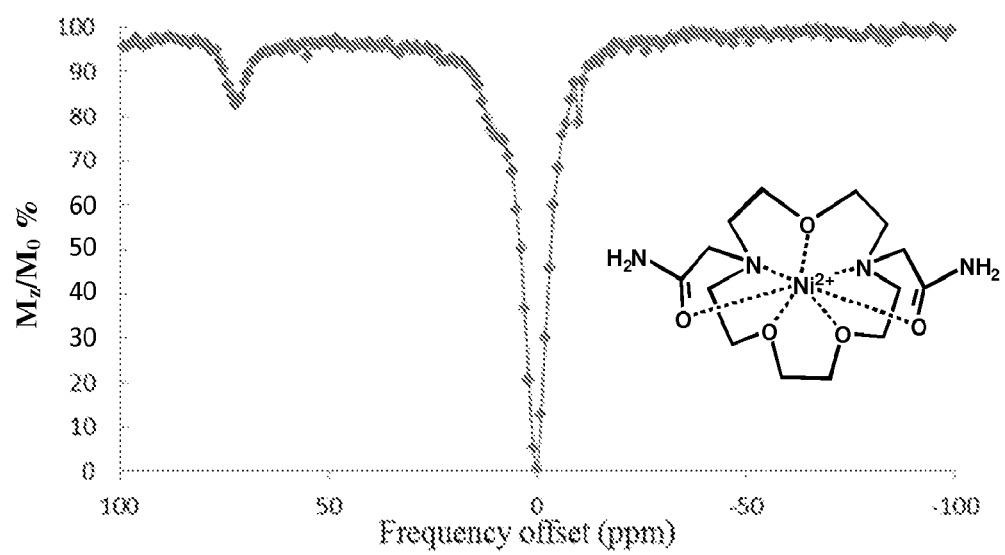
FIG. 22. Representative CEST spectrum recorded at 500 MHz of 8 mM Ni(L13) complex, 100 mM NaCl and 20 mM HEPES at pH=7.5 at 37° C. With $B_1$=1000 Hz, 2 seconds.
Figure 23:
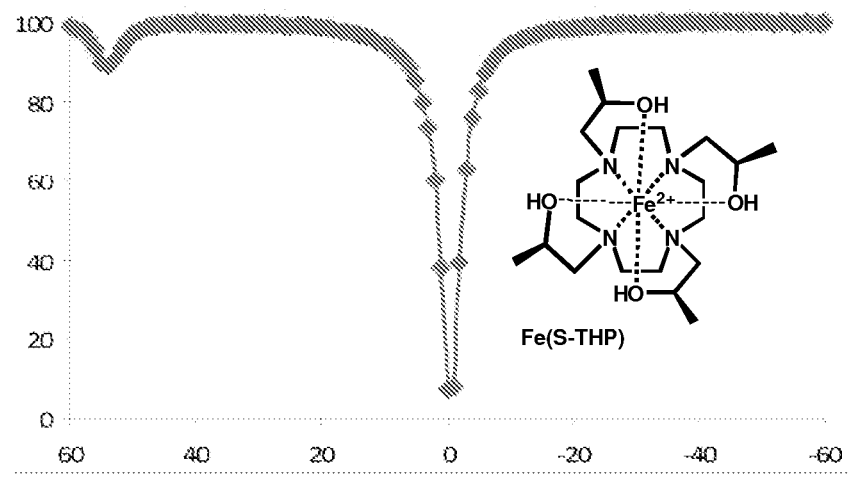
FIG. 23. Representative CEST spectrum of 10 mM Fe(L6), pH=7.3, 37° C., 100 mM NaCl, 20 mM HEPES, $B_1$=1000 Hz (25 µT) for 2 seconds.
Figure 24:
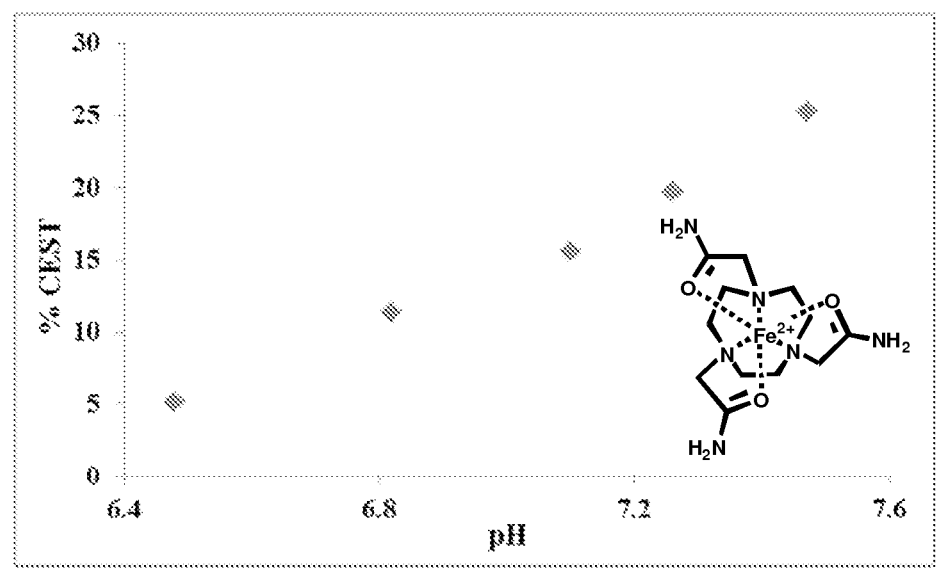
FIG. 24. Representative pH dependence of the CEST peak for Fe(L1) at 37° C., 100 mM NaCl, 20 mM buffer, $B_1$=1000 Hz (25 µT) for 2 seconds.
Figure 25:
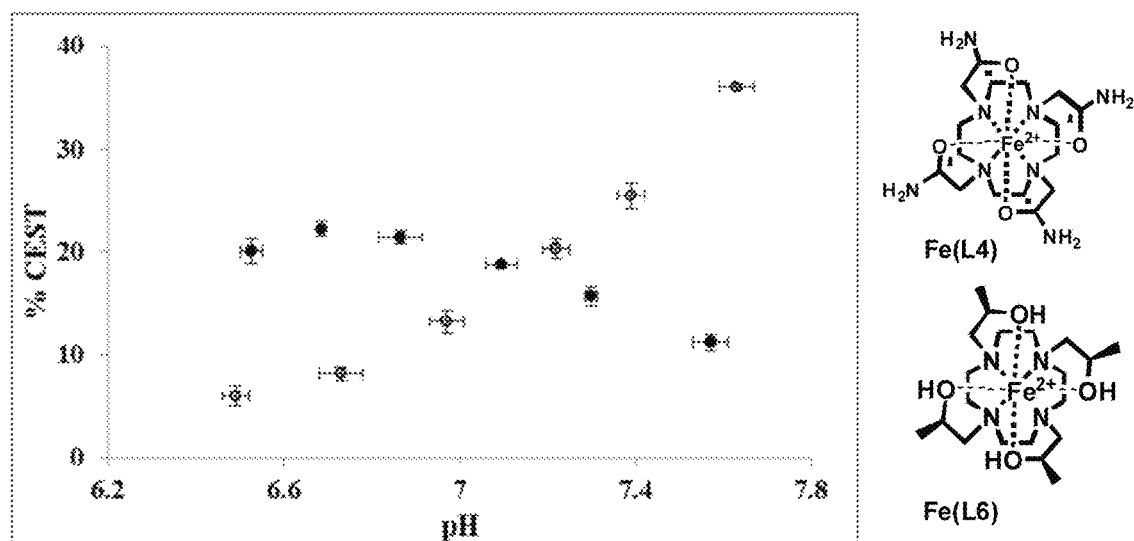
FIG. 25. Representative pH dependence of the CEST peak for Fe(L4) and Fe(L6) at 37° C., 100 mM NaCl, 20 mM buffer, $B_1$=1000 Hz (25 µT) for 2 seconds.
Figure 26:
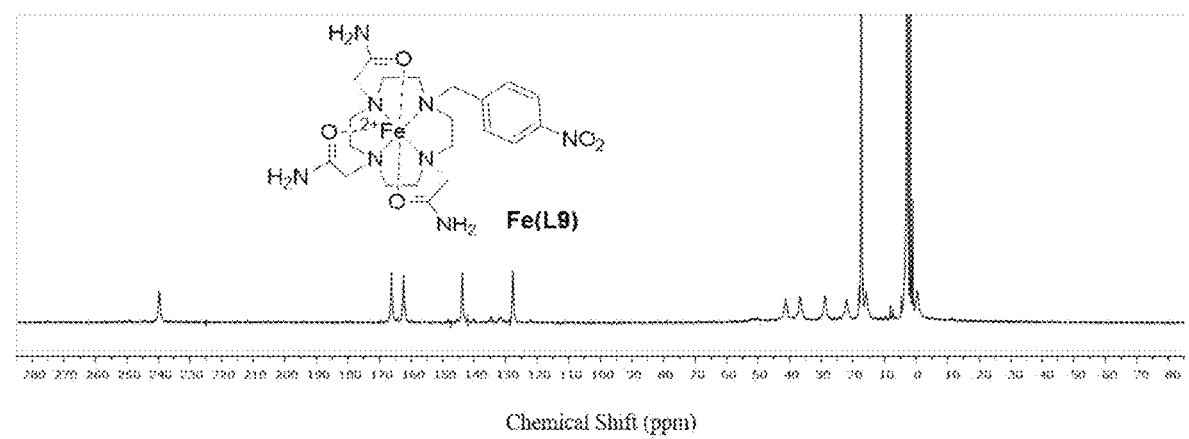
FIG. 26. Representative $^1$H NMR of Fe(L9) in $D_2O$.
Figure 27:
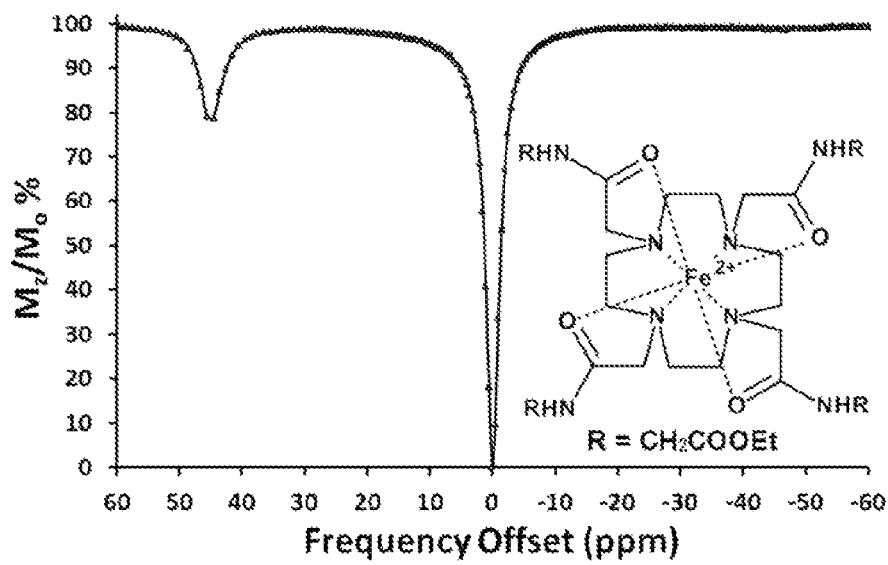
FIG. 27. Representative CEST spectrum of 60 mM Fe(L11) at pH 8.6 with $B_1$=700 Hz, 500 MHz spectrometer.
Figure 28:
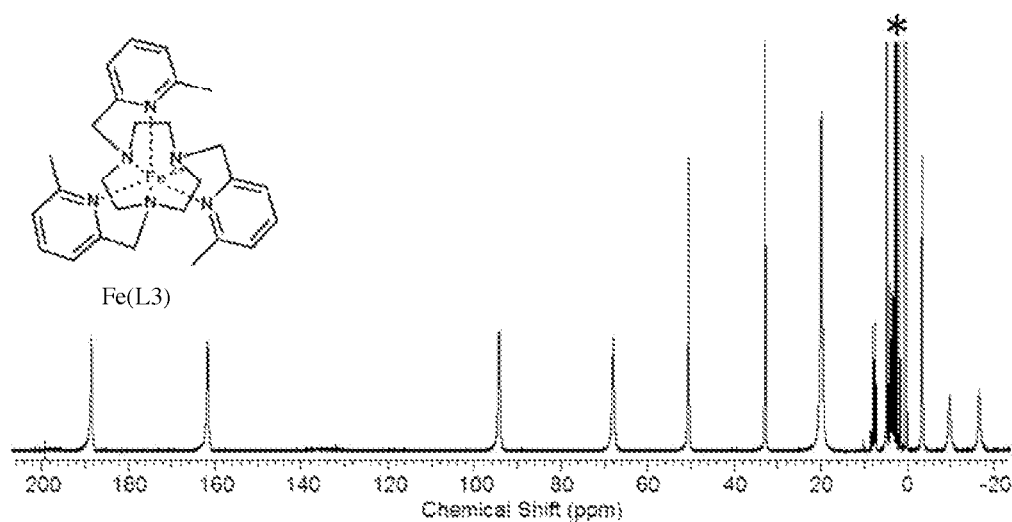
FIG. 28. Representative $^1$H NMR spectrum of Fe(L3) in $D_2O$.
Figure 29:
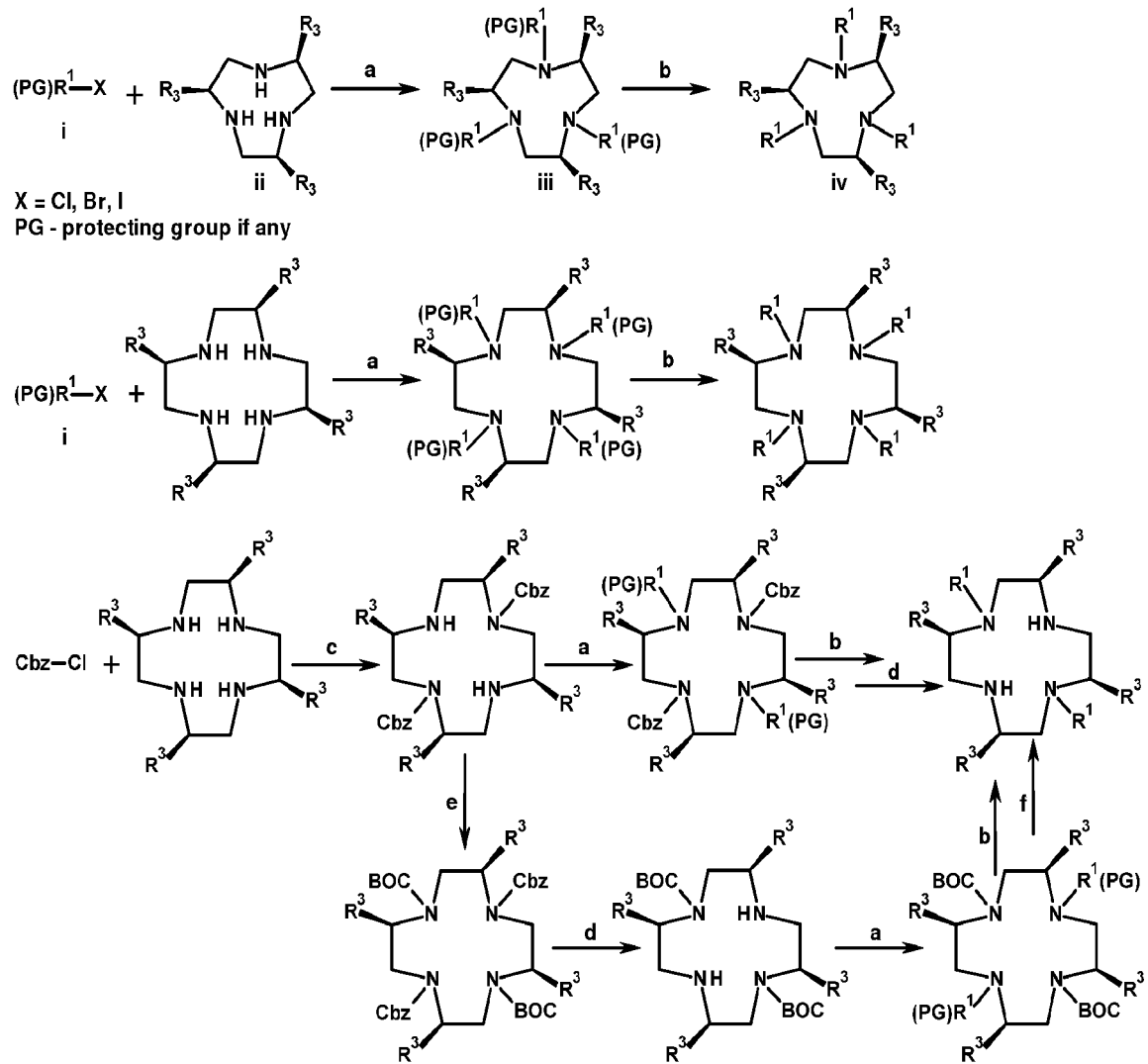
FIG. 29. Example of scheme for the synthesis of di and tetrasubstituted 1,4,7,10-tetraazacyclododecane. Reagents and conditions: a) $Et_3N$, MeOH (acetonitrile), reflux; b) deprotection; c) NaOH, dioxane-water (1:1, v/v), pH 3.5, 24 hours, room temperature; d) hydrogen, 10% Pd/C, methanol, 12 hours; e) di-t-butyl pyrocarbonate, $Et_3N$, dioxane, 0° C. to room temperature; f). trifluoroacetic acid, dichloromethane.
Figure 30:
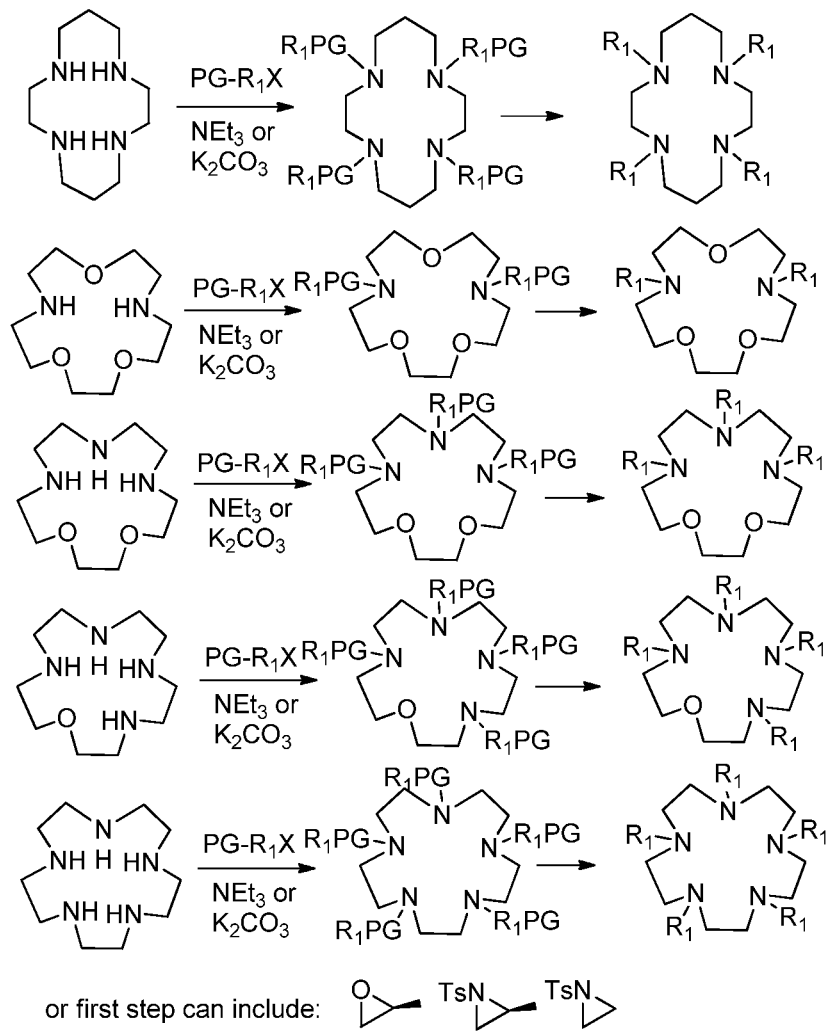
FIG. 30. Example of scheme for the addition of pendent groups to tetraaza, pentaaza macrocycles or macrocycles with both aza and ether donor groups.
Figure 31:
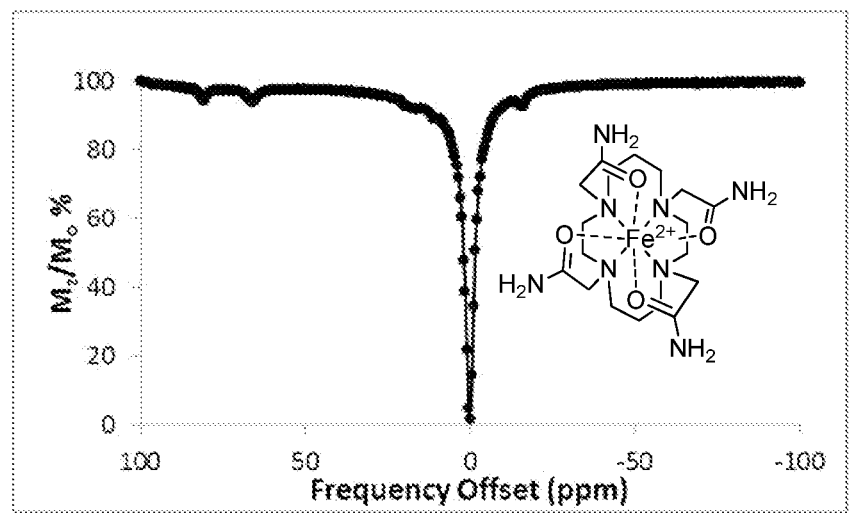
FIG. 31. Representative CEST spectrum recorded at 500 MHz of Fe(L12), 100 mM NaCl and 20 mM HEPES at pH 7.5 at 37° C. With $B_1$=1000 Hz, 2 seconds.
Figure 32:
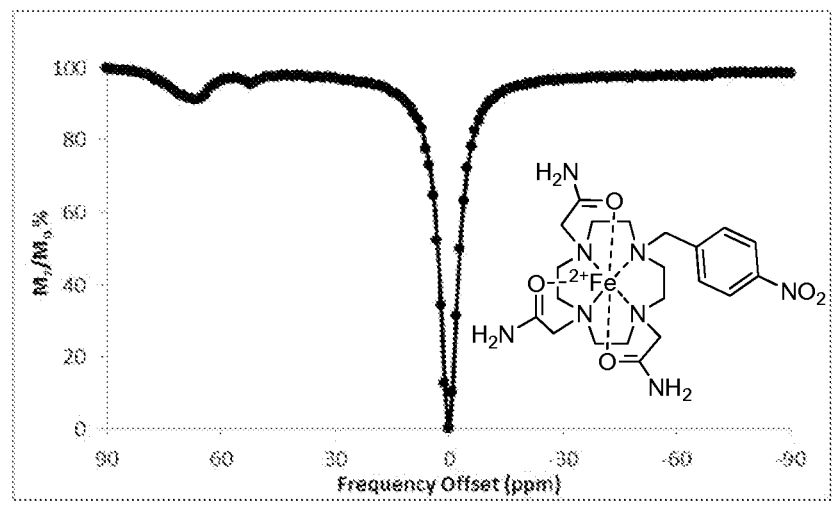
FIG. 32. Representative 28 mM Fe(L9), 20 mM HEPES, 100 mM NaCl, pH 7.2, 25° C., $B_1$=1000 Hz (25 µT) for 2 seconds.
Figure 33:
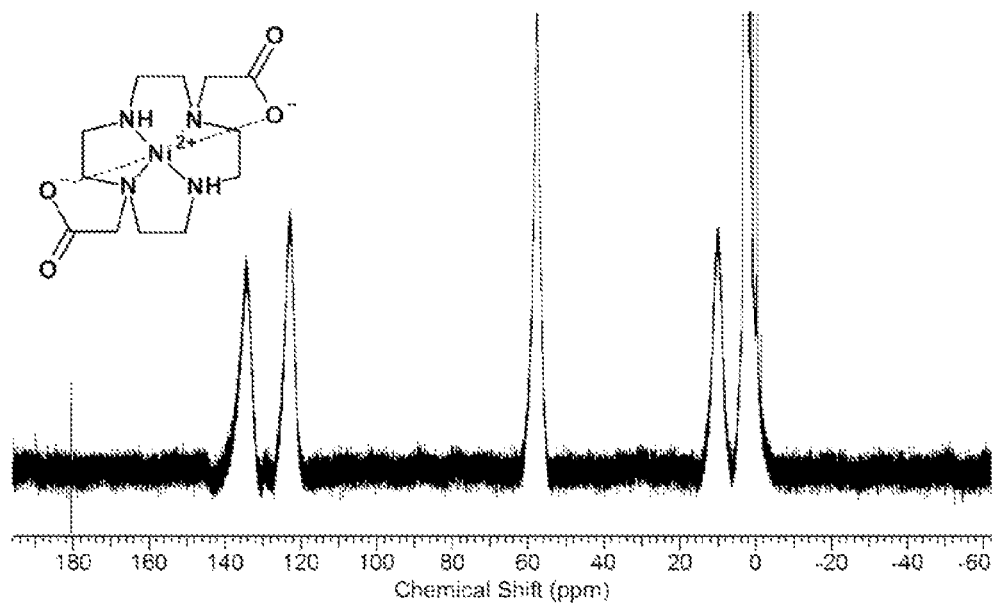
FIG. 33. Representative $^1$H NMR spectrum of Ni(L14) in $D_2O$.
Figure 34:
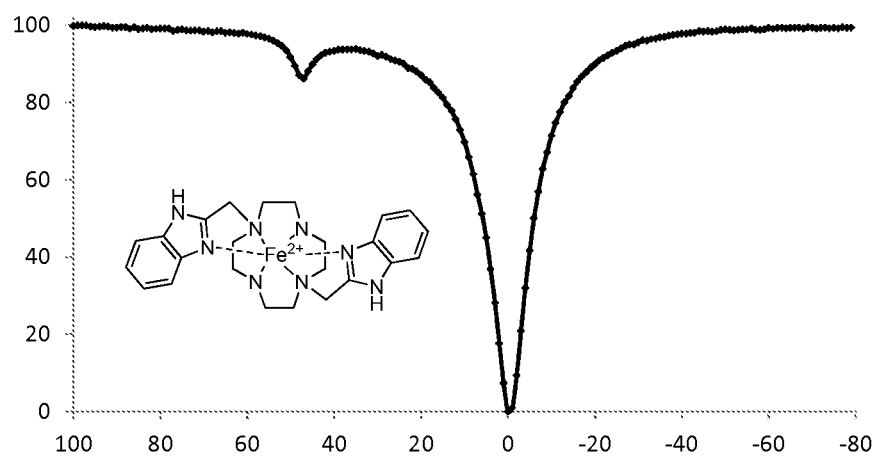
FIG. 34. Representative CEST spectrum of 5 mM Fe(L10) at pH 7.1.
Figure 35:
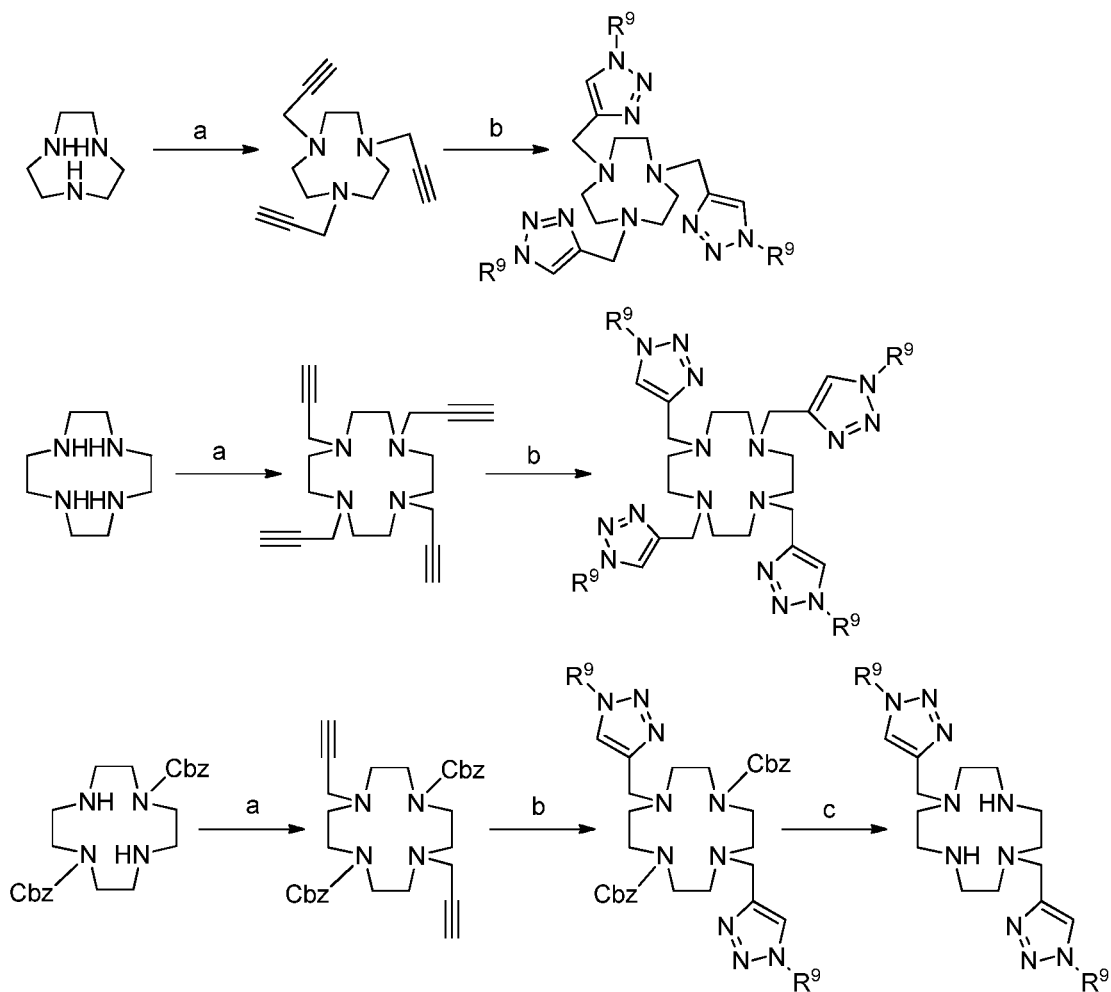
FIG. 35. Example of a reaction scheme for the synthesis of ligands with triazole pendant groups. $R^9$=H, alkyl $C_1$-$C_{12}$, PEG group, or thioether. Reagents and conditions: a) propargyl bromide, triethylamine, chloroform, 60° C.; b) $NaN_3$ or $R_9N_3$, $CuSO_4$, ascorbic acid, t-butanol-water (1:1, v/v); c) hydrogen, 10% Pd/C, methanol.
Figure 36:
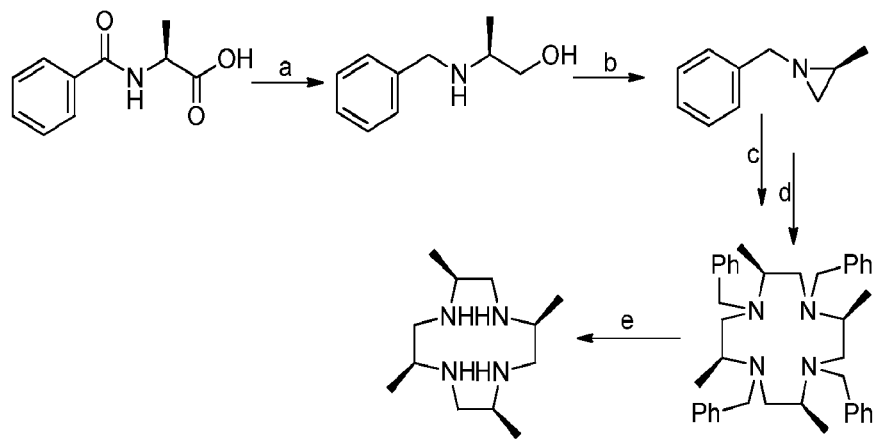
FIG. 36. Example of a CYCLEN (1,4,7,10-tetraazacyclododecane) reaction scheme for the synthesis of methylated CYCLEN derivative. Reagents and conditions: a) $B_2H_6$, THF, 0° C. to reflux, 18 hours; b) triphenylphosphine, diethyl azodicarboxylate, ether, 0° C. to room temperature; 16 hours, Ar; c) p-toluenesulfonic acid, ethanol, room temperature, 3 days; d) $NH_4OH$ (conc.), MeOH; e) ammonium formate, 20% $Pd(OH)_2$/C, EtOAc-ethanol, reflux, 16 hours.
Figure 37:
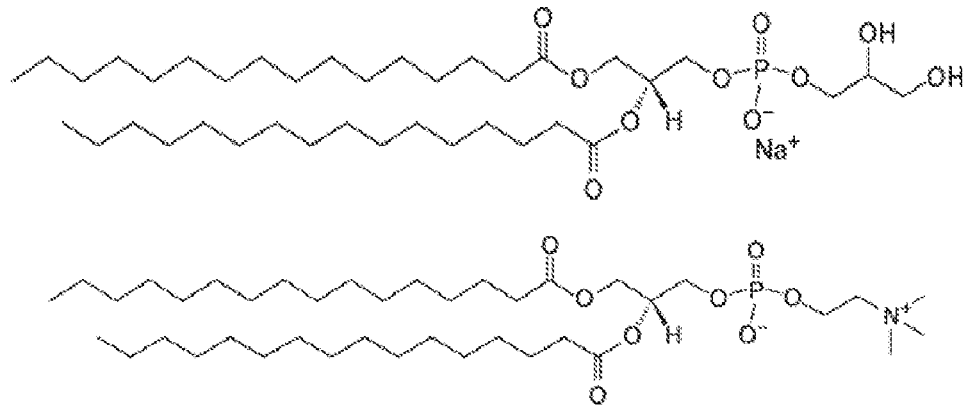
FIG. 37. Examples of phospholipid components of liposome.
Figure 38:
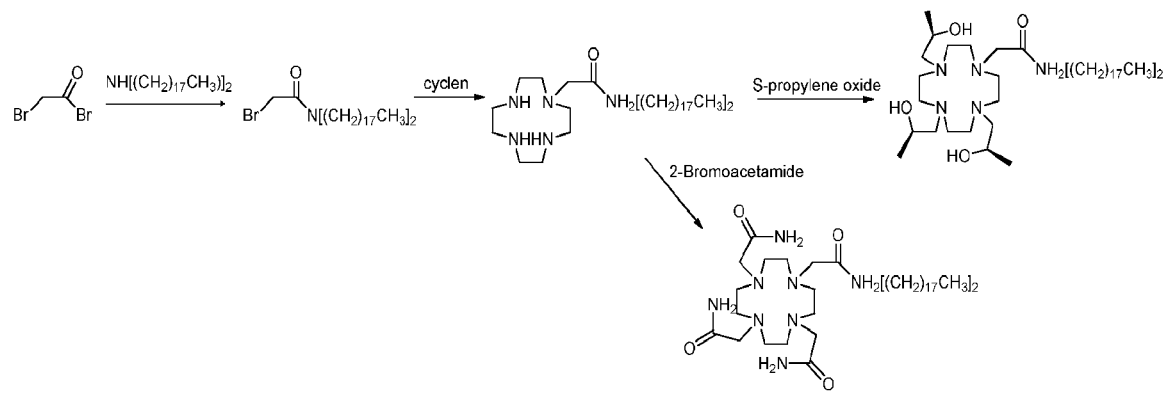
FIG. 38. Representative synthesis of a macrocycle with long alkyl chain to prepare a macrocycle for incorporation into liposome.

Ni(II) complexes containing amide groups (Ni(L1), Ni(L12) and Ni(L13)) showed CEST spectra attributed to the NH protons of the amides (FIGS. 19, 20, 22).

Figure 6:
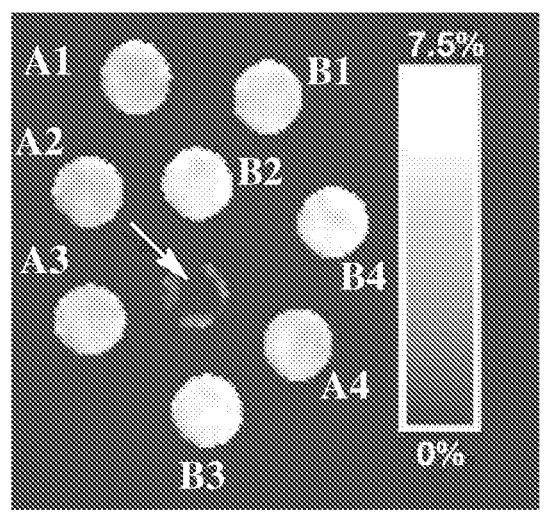
FIG. 6. Representative CEST images of phantoms on a MRI 4.7 Tesla Scanner. Arrow: buffer only, other samples contain Fe(L1) Al (pH 6.8, 2 mM), A2, (pH 6.8, 3 mM), A3 (pH 6.7, 6 mM), A4 (pH 6.8, 8 mM), B1 (pH 7.2, 2 mM) B2 (pH 7.2, 3 mM), B3 (pH 7.1, 6 mM), B4 (pH 7.1, 8 mM) at 37° C., with 20 mM HEPES (4-(2-hydroxyethyl)-1-piperazineethanesulfonic acid) and 100 mM NaCl.

To validate the observed CEST spectra of the Fe(II) complexes, CEST imaging was done at 4.7 T for a phantom array containing solutions of Fe(L1) at different concentrations as shown in FIG. 6. CEST images were acquired on a 4.7 Tesla preclinical MR scanner using a 35 mm radiofrequency coil and the ParaVision 3.0.2 research platform (Bruker Biospin, Billerica, Mass.). A pair of gradient-echo MR images were acquired at 37° C. with a pre-saturation pulse train comprised of five 1 second Gauss pulses (10 μT, 200 μs interpulse delay) either on-resonance (69 ppm) or off-resonance (−69 ppm) of the exchangeable protons. Other key acquisition parameters include: echo time/repetition time=2.1/5010 ms, flip angle=90 deg, acquisition matrix=160×160, slice thickness=2 mm, field of view=32× 32 mm, averages=1.

To determine the CEST effect, each image was normalized to the signal intensity of the buffer-only phantom and the normalized image intensity of each phantom was sampled using commercially available software (Analyze 7.0, AnalyzeDirect Inc., Overland Park, Kans.). The percent loss of signal due to paraCEST exchange was calculated using the equation: CEST Effect=1−$SI_{on}/SI_{off}$, where $SI_{on}$ is the image intensity of each sample acquired with an on-resonance pre-saturation pulse and $SI_{off}$ is the image intensity acquired with the off-resonance pre-saturation pulse. To create the CEST image (FIG. 6), each data set was first filtered with a spatial low-pass filter (kernel size: 5×5) to improve signal-to-noise, normalized by image intensity of the buffer-only phantom, and then subtracted. Phantoms in the subtraction image were isolated using binary masking techniques, and a "hot-iron" pseudo-color lookup table was applied to enhance visual detection of differences of the CEST effect in phantoms.

The wells labeled A1-A4 and B1-B4 (FIG. 6) contained solutions of Fe(L1) with NaCl and buffer at acidic (A) or basic (B) pH. The phantoms show that CEST increases linearly with concentration of the Fe(II) complex and improves at basic pH.

Additional ligand considerations. Pendent groups for macrocycles. There are many additional donor groups with exchangeable protons that would form Fe(II) paraCEST agents (FIG. 1). Alcohol donor groups, used successfully with Ln(III) paraCEST agents, may also form Fe(II) paraCEST agents (L6). It has been shown that pyridine pendent groups with amine substituents bind to Fe(II) to form paraCEST agents. Variations include different amino group positions on the pyridine ring (L2, L8). Alternately, amides, alcohols or carboximidamide groups could be used (L4, L6, L11).

Materials and methods. Instrumentation. All $^1$H NMR spectra were acquired using Varian NMR spectrometers operating at 500, 400, and 300 MHz. Chemical shifts were referenced to residual solvent peaks. Mass spectral data were acquired on a ThermoFinnigan LCQ Advantage IonTrap LC/MS equipped with a Surveyor HPLC system. High-resolution mass spectral data were acquired on a ThermoFinnigan MAT95XL w/ESI II source (NSF Award HE0091977). CEST experiments were acquired on an Inova-400 Spectrometer at room temperature. The pulse power was varied with an irradiation time of 2 or 4 seconds.

The Evans' method was used to determine the effective magnetic moment in the solution state. An insert containing the paramagnetic sample and t-butanol was used against a reference outer lock of D$_2$O containing t-butanol as well.

$$X_g = \frac{-3\Delta f}{4\pi f m} + X_o + \frac{X_o(d_o - d_s)}{m} \qquad \text{Eq. 4}$$

Here $\chi_g$ is mass susceptibility of the solute (Fe(L1) or Fe(L2)) in cm$^3$/g, $\Delta f$ is the observed frequency shift between diamagnetic and paramagnetically shifted reference standard, t-butanol, in Hz. The value for f is the spectrometer frequency in Hz, m is the mass of substance (per cm$^3$ of solution), $\chi_o$ is the mass susceptibility of the solvent (cm$^3$/g). The third term may be neglected, but if included, d$_o$ is the density of the solvent in g/cm$^3$, d$_s$ is density of the solution, g/cm$^3$. The $\chi_g$ solution to the above can be converted to $\chi_m$, the molar susceptibility (cm$^3$/mol), by multiplying by the molecular weight of the paramagnetic complex. From this, the effective magnetic moment can be determined:

$$\mu = 2.84(\chi_m T)^{1/2} \qquad \text{Eq. 5}$$

Where μ is effective magnetic moment and T is temperature in Kelvin. From these calculations, an effective magnetic moment of 5.1 Bohr-Magnetons for Fe(L1) and 5.8 Bohr-Magnetons for Fe(L2) at 25° C. was obtained.

Reversed-phase high-performance liquid chromatography (HPLC) purification runs were accomplished using Waters 1525 Binary HPLC Pump equipped with a Waters 2487 Dual Absorbance Detector system. Compound L2 was HPLC-purified using preparative C8 column (7 μm, 19×150 mm) A linear gradient of solvent B (0.1% TFA in methanol) in solvent A (0.1% TFA in water) at constant flow rate of 8 mL/min was used for HPLC purification.

Synthetic Methods. 1,4,7-Tris(carbamoylmethyl)-1,4,7-triazacyclonone (L1) was prepared as reported previously. MES buffer was used at pH 5.5 to 6.5 and HEPES buffer was used at pH 6.5 to 7.5. Tris(2-pyridylmethyl)-1,4,7-triazacyclonone (L3) was synthesized according to the reported procedure.

Synthesis of 6-(bromomethyl)-2-methyl-3-nitropyridine (ii). 3-Nitro-2,6-lutidine i (2.50 g, 16.5 mmol, 1 equiv.) was dissolved in 200 mL of argon-purged carbon tetrachloride. The reaction mixture was heated to 50° C. under argon. AIBN (0.14 g, 0.83 mmol, 5 mol %) was added to the reaction mixture in one portion under constant stirring, followed by the addition of NBS (2.93 g, 16.5 mmol, 1 equiv.) in small portions over a period of 2 hours. The reaction mixture was further refluxed for 8 hours at constant stirring and under light irradiation. Once the reaction was complete, solvent was removed in vacuo producing a brownish residue. This residue was suspended in a mixture of methanol-dichloromethane, in which non-dissolved solids were removed by filtering through a SiO$_2$ plug (ca. 120 mL) using an eluent of methanol-dichloromethane (1:20 v/v). Fractions containing ii were combined and solvent was removed in vacuo. Resultant oil was subject to SiO$_2$ column chromatography using a mixture of ethyl acetate (gradient from 2% to 10%) in hexanes as an eluent. Fractions containing product were concentrated in vacuo producing analytically pure ii. Yield: 0.41 g, 1.78 mmol, 11%. $^1$H NMR, 500 MHz (CDCl$_3$, ppm): δ=8.26 d (1H, Ar, J=9 Hz), 7.47 d (1H, Ar, J=9 Hz), 4.52 s (2H, CH$_2$), 2.83 s (3H, CH$_3$). $^{13}$C NMR, 75 MHz (CDCl$_3$, ppm): δ=160.46, 153.73, 144.66, 133.66, 121.61, 32.07, 23.84. ESI-MS (m/z): [M+H]$^+$, calculated: 231.0, found: 231.0.

Synthesis of 1,4,7-tris R6-methyl-5-nitro-2-pyridyl) methyl]-1,4,7-triazacyclononane (iv). 1,4,7-Triazacyclononane iii (41 mg, 0.32 mmol, 1 equiv.) and alkylating agent ii (258 mg, 1.12 mmol, 3.5 equiv.) were dissolved in 8 mL of dry acetonitrile followed by addition of triethylamine (180 μL, 1.29 mmol, 4 equiv.). The reaction mixture was stirred at 50° C. for 24 hours under argon. Upon completion of the reaction, solvent was removed in vacuo producing a brown oily residue. The crude product was purified by reversed-phase HPLC using a gradient of solvent B from 30% to 70% in solvent A over 40 min. ESI-MS analyses of fractions with retention time t$_R$=21 min confirmed product iv. These fractions were combined and solvent was removed by lyophilization producing iv in the form of TFA salt. Yield: 80 mg, 63 μmol, 20%. $^1$H NMR, 500 MHz (CD$_3$OD, ppm): δ=8.35 d (3H, Ar, J=9 Hz), 7.55 d (3H, Ar, J=9 Hz), 4.32 s (6H, 3CH$_2$), 3.23 m (12H, 6CH$_2$), 2.78 s (9H, 3CH$_3$). $^{13}$C NMR, 75 MHz (CD$_3$OD, ppm): δ=160.60, 154.51, 146.59, 134.91, 123.40, 60.07, 50.74, 23.92. High-resolution ESI-MS (m/z): [M+H]$^+$, calculated: 580.2627, found: 580.2691.

Synthesis of 1,4,7-tris[(5-amino-6-methyl-2-pyridyl) methyl]-1,4,7-triazacyclononane (L2). TFA salt of compound iv (80 mg, 63 μmol) was dissolved in 40 mL of methanol containing 21 mg (11 mol %) of 10% Pd/C. Reduction of nitro groups was carried out in a Parr hydrogenation apparatus for 8 hours using hydrogen gas. Once reduction was complete, the reaction mixture was filtered through Celite. The solvent was removed in vacuo producing yellow oil. The crude product was HPLC-purified using a gradient of solvent B (5% to 35%) in solvent A over 30 min ESI-MS analyses of fractions with retention time t$_R$=11 min confirmed product L2. These fractions were combined and solvent was removed by lyophilization producing L2 in the form of TFA salt. The product was further desalted by passing through 2 mL of Dowex® 1×2-100 strongly basic anion exchange resin. The resulting aqueous solution was concentrated in vacuo producing L2. Yield: 12.6 mg, 26 μmol, 41%. $^1$H NMR, 500 MHz (D$_2$O, pH 7.0, ppm): δ=7.10 d (3H, Ar, J=9 Hz), 6.77 d (3H, Ar, J=8 Hz), 3.77 s (6H, 3CH$_2$), 2.75-2.95 m (12H, 6CH$_2$), 2.35 s (9H, 3CH$_3$). High-resolution ESI-MS (m/z): [M+H]$^+$, calculated: 490.3374, found: 490.3385.

Table 1. Acid-dissociation constants (pK$_a$) and ligand-Fe (II) equilibrium constants for L1 and L3 for solutions containing 1.05 mM of L1 or L3 and 1.0 mM Fe(OTf)$_2$, 0.10 M NaCl, at 25° C.

TABLE 1

| Equilibrium | Fe(L1) | Fe(L3) |
|---|---|---|
| Log $K_1$ | 10.19 ± 0.11 | 12.20 ± 0.81 |
| Log $K_2$ | <2 | 4.6 ± 0.50 |
| Log $K_3$ | <2 | <2 |
| Log $K_4$ | N/A | <2 |
| Log $K_5$ | N/A | 3.93 ± 0.64 |
| Log $K_6$ | N/A | 2.33 ± 0.21 |
| Log $K_{Fe-L}$ | 13.47 ± 0.25 | 19.24 ± 0.64 |
| Log $K_{Fe-LH}$ | 5.54 ± 0.14 | 4.8 ± 0.87 |
| Log $K_{FeL-OH}$ | 9.43 ± 0.18 | 10.15 ± 1.35 |

TABLE 2

Equilibrium Expressions for L = L1 or L2. Equilibrium constants were derived from fitting the data to Hyperquad 2008. Shown below in Table 2 are equilibrium constants and expressions.

| | |
|---|---|
| Eq. 1 | $L + H^+ \leftrightarrows LH^+$ |
| | $K_1 = [LH^+]/([L][H^+])$ |
| Eq. 2 | $LH^+ + H^+ \leftrightarrows LH_2^{2+}$ |
| | $K_2 = [LH_2^{2+}]/([LH^+][H^+])$ |
| Eq. 3 | $LH_2^{2+} + H^+ \leftrightarrows LH_3^{3+}$ |
| | $K_3 = [LH_3^{3+}]/([LH_2^{2+}][H^+])$ |
| Eq. 4 | $LH_3^{3+} + H^+ \leftrightarrows LH_4^{4+}$ |
| | $K_4 = [LH_4^{4+}]/([LH_3^{3+}][H^+])$ |
| Eq. 5 | $LH_4^{4+} + H^+ \leftrightarrows LH_5^{5+}$ |
| | $K_5 = [LH_5^{5+}]/([LH_4^{4+}][H^+])$ |
| Eq. 6 | $LH_5^{5+} + H^+ \leftrightarrows LH_6^{6+}$ |
| | $K_6 = [LH_6^{6+}]/([LH_5^{5+}][H^+])$ |
| Eq. 7 | $L + Fe^{2+} \leftrightarrows FeL^{2+}$ |
| | $K_{FeL} = [FeL^{2+}]/([Fe^{2+}][L])$ |
| Eq. 8 | $FeL^{2+} + H^+ \leftrightarrows FeLH^{3+}$ |
| | $K_{FeLH} = [FeLH^{3+}]/([FeL^{2+}][H^+])$ |
| Eq. 9 | $FeL^{2+} + OH^- \leftrightarrows FeL-OH^+$ |
| | $K_{FeL-OH} = [FeL-OH^+]/([FeL^{2+}][OH^-])$ |

Example 2

Example of Fe(II) and Ni(II) macrocyclic compounds and CEST and MRI paraCEST agents.

Fe(II) macrocyclic complexes. Fe(II) paraCEST agents were developed by preparing ligands that stabilize Fe(II), contain multiple exchangeable protons to enhance the CEST effect and form six, seven or eight coordinate complexes to protect the Fe(II) from binding additional ligands that might complicate the CEST signal. In FIG. 1 shown are macrocyclic ligands based on either 1,4,7-triazacyclonone or 1,4,7,10-tetraazacyclododecane. Pendent groups are highly variable and include nitrogen heterocycles such as pyridine, pyrazole and imidazole or aliphatic amines or alcohol groups. All ligands are chosen to stabilize Fe(II) oxidation state and contain ligands with exchangeable OH or NH groups.

Figure 12:
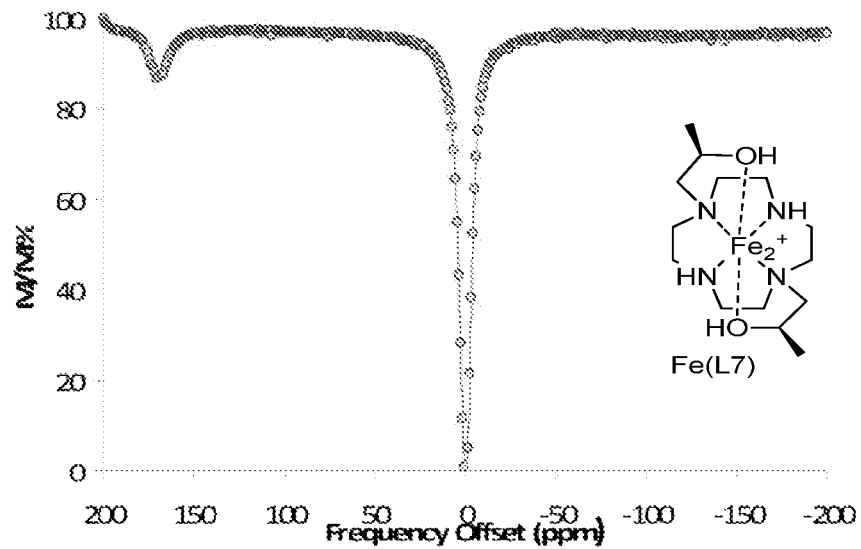
FIG. 12. Example of CEST spectrum of 25 mM complex Fe(L7) at pH 6.0, 100 mM NaCl, B$_1$=1000 Hz at 37° C., 400 MHz spectrometer.
Figure 13:
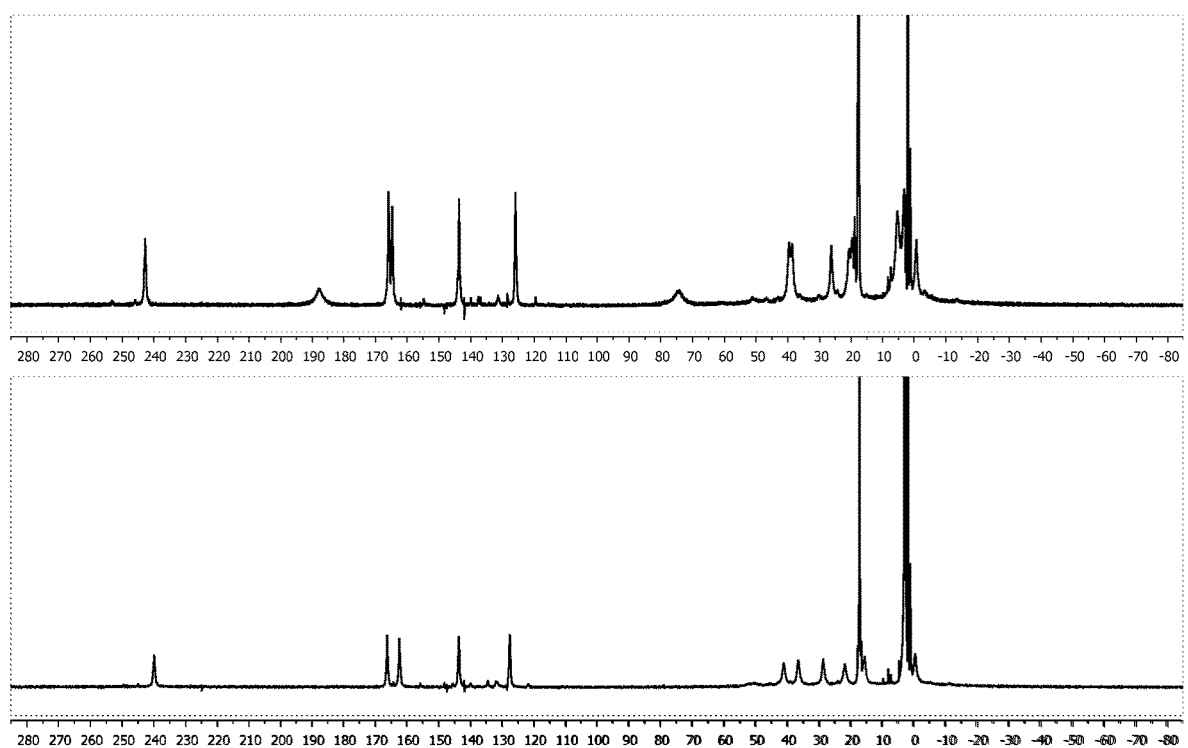
FIG. 13. Representative $^1$H NMR spectrum of Fe(L7) showing highly shifted proton resonances. Top is in d$_3$-acetonitrile and bottom is the same sample with a few drops D$_2$O. The resonances that disappear are attributed to the alcohol and amine protons. The sharp proton resonances of this complex in combination with its paraCEST properties in FIG. 13 shows that Fe(L7) is suitable as a dual paraCEST/chemical shift agent for thermometry.

CEST spectra, plotted as the percent reduction of the water proton resonance as a function of the presaturation frequency are shown for (Fe(L9) and Fe(L7) in FIGS. 12-13. Also shown is the proton NMR spectrum of Fe(L7) to demonstrate the relatively sharp proton resonances of this compound (FIG. 13). These sharp resonances in combination with the highly shifted CEST peak at 170 ppm make this a very promising candidate for the development of dual paraCEST/chemical shift contrast agents.

Generally, macrocyclic complexes in FIG. 1 are prepared from the macrocycle and Fe(II) salt such as $FeCl_2$, or $Fe(CF_3SO_3)_2$ in acetonitrile at room temperature with argon bubbled through the solvent. This helps to ensure that a negligible amount of $O_2$ is present in the reaction flask. In the absence of an inert atmosphere, difficulties in maintaining the desired oxidation state may arise through mechanisms such as oxidation of the metal to Fe(III) prior to complexation with the ligand. Once Fe(II) is complexed by the macrocyclic ligands, the high-spin (HS) Fe(II) state is maintained over several days in neutral $D_2O$ solution at room temperature, as evidenced by persistent $\mu_{eff}$ values.

Figure 15:
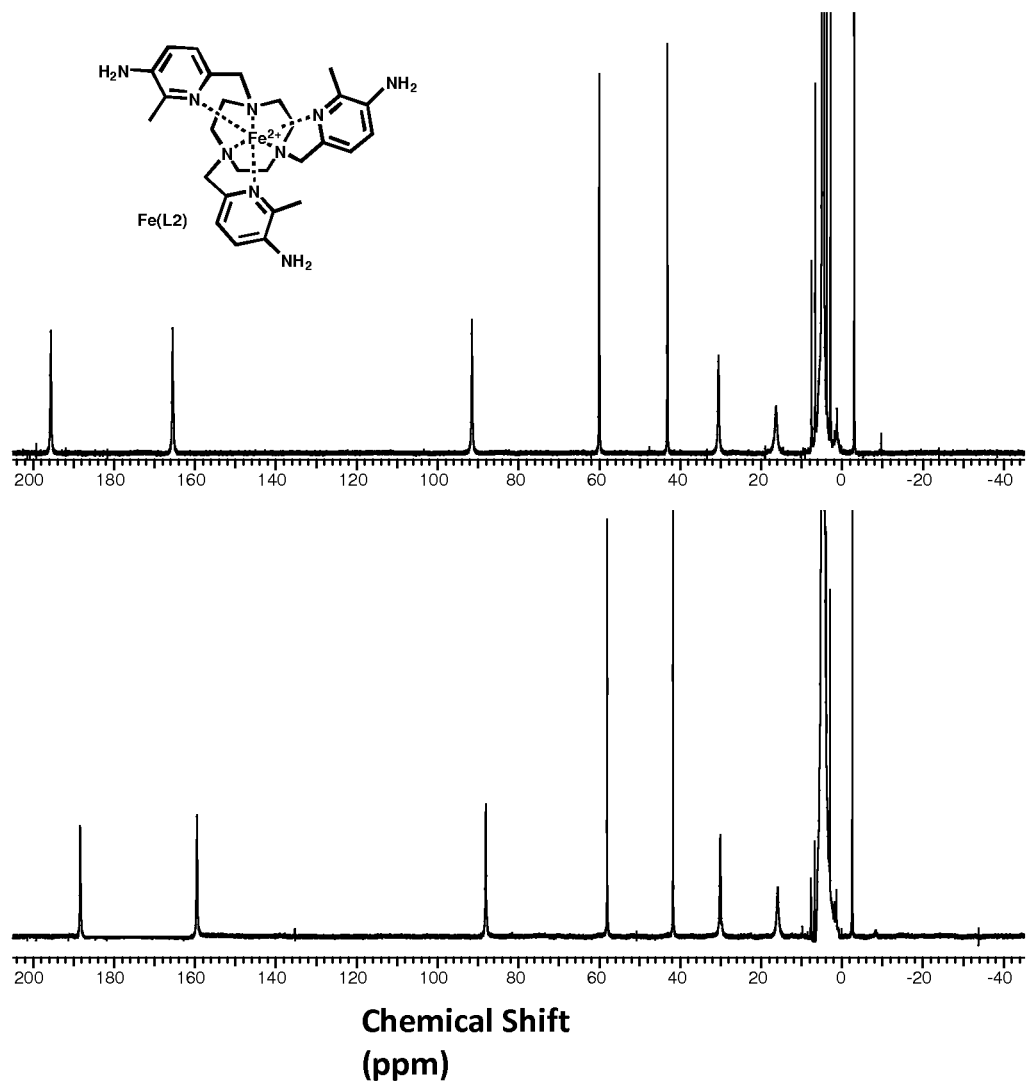
FIG. 15. Representative $^1$H NMR of Fe(L2) in D$_2$O showing the temperature dependence of the non-exchangeable protons from 25° C. (top) to 37° C. (bottom).
Figure 16:
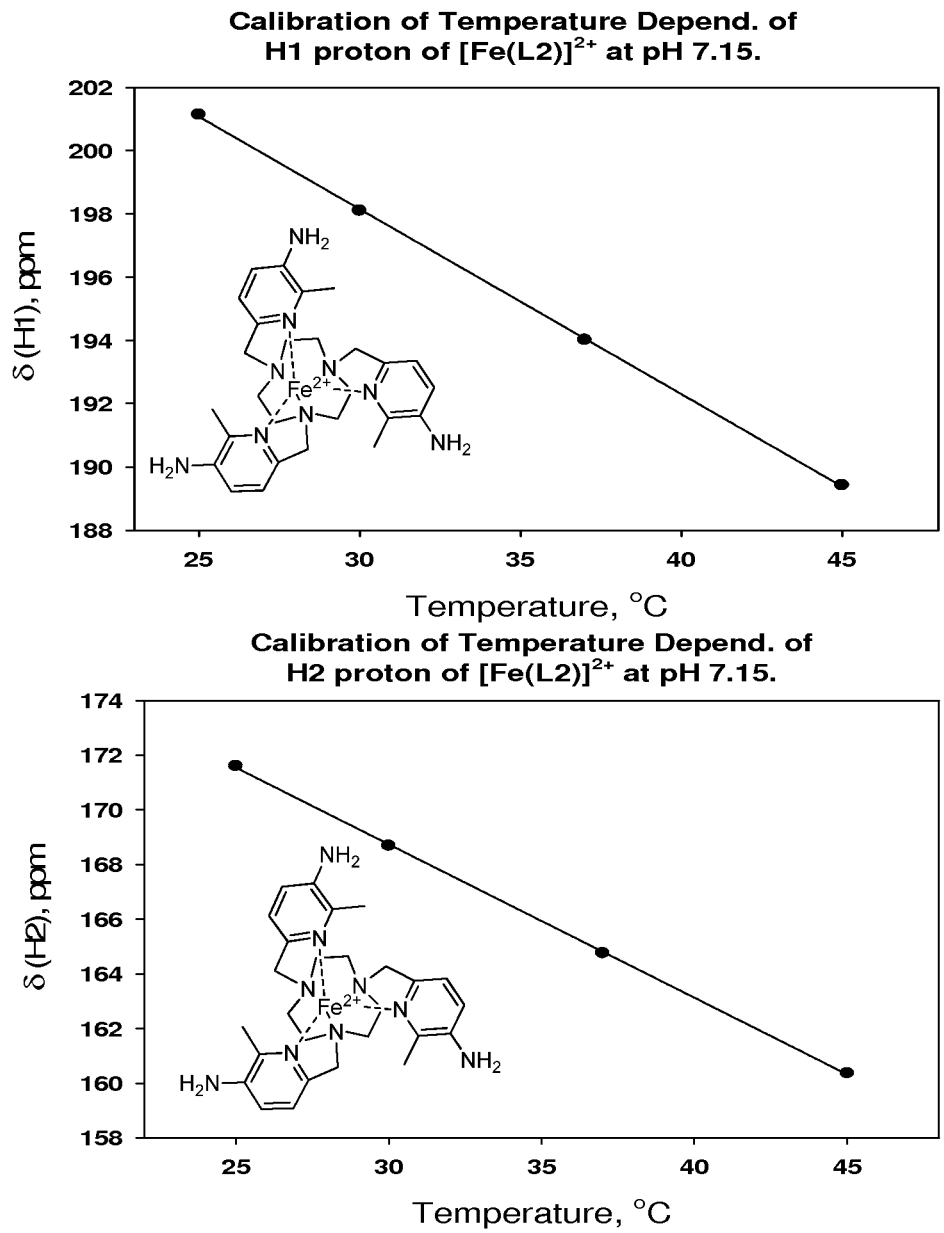
FIG. 16. Representative temperature dependence of two different proton resonances of a Fe(L2) complex.
Figure 17:
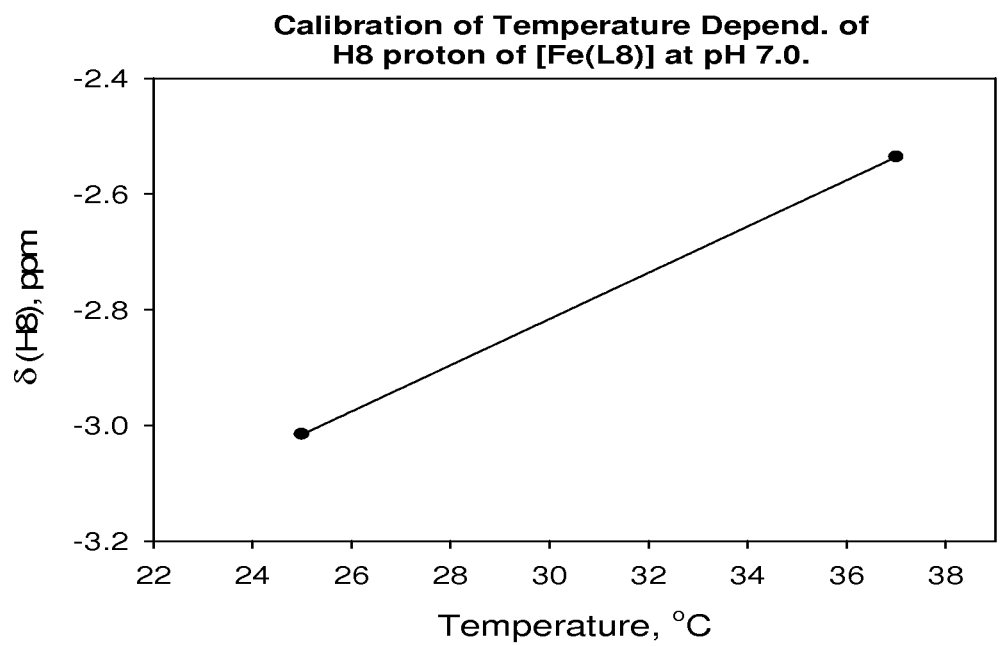
FIG. 17. Representative temperature dependence of the most shifted proton resonance of a Fe(L8) complex.
Figure 18:
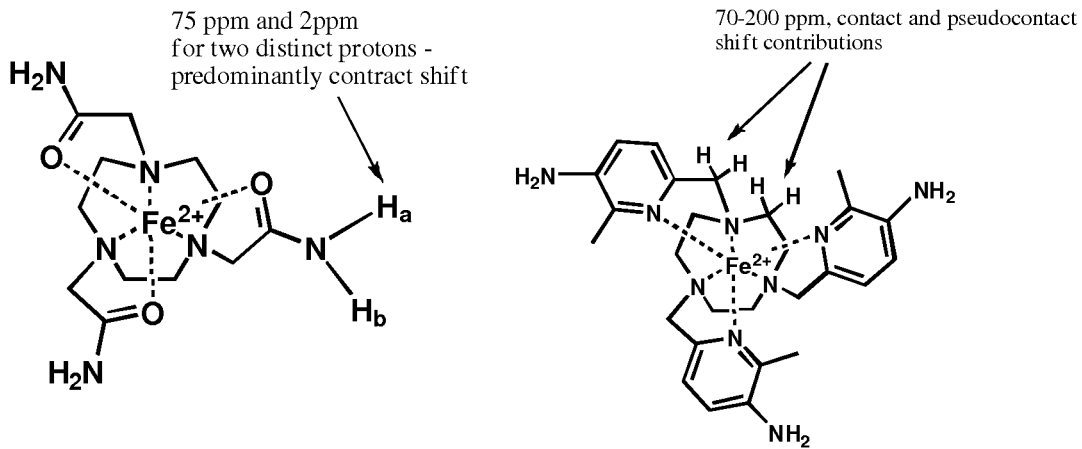
FIG. 18. The two protons on the amide are chemically inequivalent because there is restricted rotation about the CN bond. These two protons have chemical shifts that vary by about 70 ppm. Theoretical calculations show that the large chemical shift difference is due to paramagnetic contact (through bond) shift contributions. The paramagnetic induced shifts of the aliphatic CH protons of the complex are a mixture of contact and pseudocontact shifts.

Chemical shift imaging and thermometry. Preliminary data shows that the non-exchangeable proton resonances of Fe(L2) and Fe(L3) are remarkably sharp (250 Hz) for paramagnetic complexes and shift as a function of temperature (FIGS. 15-17). These complexes are ideal for development as a temperature dependent MRS agent for an application known as thermometry—temperature sensing in vivo. The best thermometry agents have large temperature coefficients (CT, chemical shift change per degree=$\Delta\delta$/° C.) and narrow linewidths (FWHM) to distinguish small temperature changes of 0.5° C. The most useful parameter is CT/FWHM which takes into account both shift with temperature and linewidth. A value of 1.80 is obtained for the best Ln(III) sensors. One of the Fe(L2) proton resonances has a CT/FWHM of 2.44, better than the best Ln(III) complex reported to date (Table 3).

TABLE 3

Summary of temperature dependent properties of iron(II) macrocyclic complexes in comparison to lanthanide(III) complexes.

| Complex | CT (ppm/° C.) | FWHM | CT/FWHM | Δ (ppm) |
|---|---|---|---|---|
| Tb(DOTAMP) | 1.44 | 1.25 | 1.18 | −287 |
| Tm(DOTAMP) | −1.44 | 0.800 | 1.80 | 224 |
| Fe(L11) | 0.610 | 0.250 | 2.44 | 195 |
| Fe(L2) | 0.594 | 0.388 | 1.53 | 201 |

Preliminary experiments showed that the proton chemical shifts of Fe(L2) are independent of pH from pH 6.5-8, as expected because there are no ionizable groups over this pH range. Previously reported paramagnetic Ln(III) complexes that show proton chemical shift changes with pH have donor groups such as phosphonate that ionize to change the donor strength and shift the proton resonances by changing the primary coordination sphere. Complexes that show chemical shift changes with both pH and temperature may find application as BIRDS agents (BIRDS—biosensor imaging of redundant deviation of shifts).

TABLE 4

Electrochemical potentials and reactive oxygen species generation by Fe(II) complexes.

| Complex | Ascorbate consumption[a] ×10⁻⁵ (s⁻¹) | Benzoate hydroxylation[b] % standard | % dissociation over 12 hours | E° vs. NHE (mV)[d] |
|---|---|---|---|---|
| Fe(L1) | 7.2 ± 0.96 | 8.2 ± 0.9 | <9% | 860 ± 9 |
| Fe(L3) | 2.4 ± 0.75 | 10 ± 1.6 | 1% (24 hours) | 930 ± 10 |
| Fe(L4) | 4.0 ± 1.0 | 3.5 ± 0.2 | 0% | 800 ± 5 |
| Fe(EDTA) | 77 ± 13 | 88 ± 2.5 | — | 390 |
| Fe(II) | 9 ± 2.4 | 3.4 ± 0.5 | — | 77[e] |

[a] 100 μM ascorbate, 10 μM Fe(II), 10 μM ligand, 10 mM HEPES, pH 7.4 at 37° C.
[b] 10 μM complex, 1.00 mM benzoate, 50 μM ascorbate, 50 μM H₂O₂, 100 mM NaCl, 20 mM HEPES, pH 7.5 at 37° C. for 1 hr.
c. 10 μM Fe(II) complex, 50 μM ascorbate, 50 μM H₂O₂, 100 mM NaCl, 20 mM HEPES, pH 7.5 at 37° C. for 2 hrs. Numbers in parentheses are from experiments run in 5% DMSO.
[d] 100 mM tetrabutylammonium hexafluorophosphate in acetonitrile
[e] Value in water.

TABLE 5

| Complex | paraCEST peak (ppm) | MRSI (narrow proton resonances) | resistance to dissociation >12 h, neutral pH |
|---|---|---|---|
| Fe(L1) | 69 | No | Moderate |
| Fe(L2) | 6 | Yes | good |
| Fe(L3) | None | Yes | excellent |
| Fe(L4) | 50 | No | excellent |
| Fe(L5) | 52 | Possible | moderate |
| Fe(L6) | 54 | Possible | Moderate |
| Fe(L7) | 170 | Yes | moderate |
| Fe(L8) | No | Yes | good |
| Fe(L11) | 45 | No | excellent |
| Ni(L1) | 76 | No | good |
| Ni(L12) | 77 | No | good |
| Ni(L13) | 73 | Yes | poor |

While the invention has been particularly shown and described with reference to specific embodiments (some of which are preferred embodiments), it should be understood by those having skill in the art that various changes in form and detail may be made therein without departing from the spirit and scope of the present invention as disclosed herein.

What is claimed is:

1. A macrocyclic compound having a macrocyclic core having the following structure:

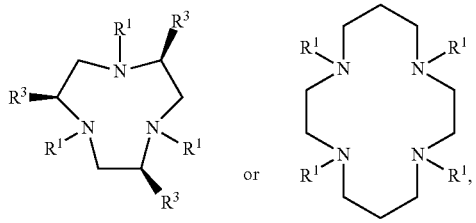

wherein
each $R^3$ is independently selected from H and $CH_3$, and
$R^1$ is a pendant group independently selected from the group consisting of: —H, —$CH_3$,

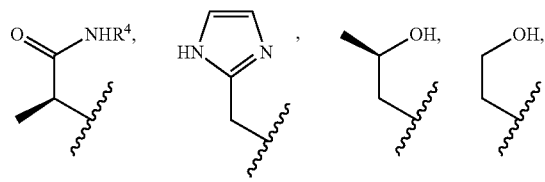

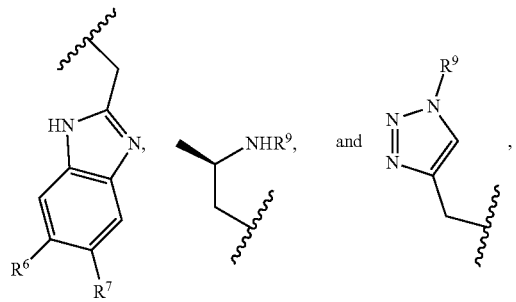

wherein each $R^4$ is independently selected from the group consisting of H, $C_1$ to $C_{12}$ alkyl groups, PEG groups, thioether groups, and $CH_2CO_2R^8$, $R^6$ is H or $OCH_3$, $R^7$ is H, $OCH_3$, or $CO_2H$, each $R^8$ is independently selected from the group consisting of $C_1$ to $C_{12}$ alkyl groups, PEG groups group, and thioether groups, and each $R^9$ is independently selected from the group consisting of H, $C_1$ to $C_{12}$ alkyl groups, PEG groups group, and thioether groups;

the macrocyclic compound has at least one exchangeable proton; and a Fe(II) or Ni(II) cation is complexed to the macrocyclic core and/or at least one pendant group of the macrocyclic compound, wherein the complexed Fe(II) is high spin Fe(II), with the proviso:

i) that when a high-spin Fe(II) cation is complexed with the macrocyclic core, the macrocyclic core does not have the following structure:

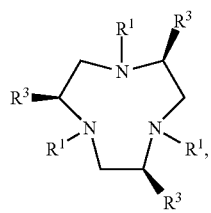

wherein each $R^3$ is H and each $R^1$ is

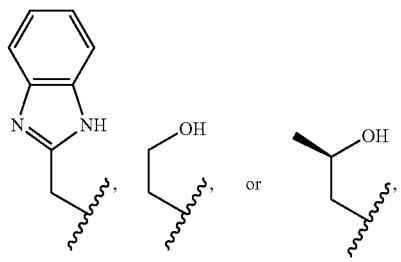

and ii) that when a Ni(II) cation is complexed with the macrocyclic core, the macrocyclic core does not have the following structure:

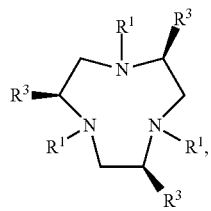

wherein each R³ is H and each R¹ is

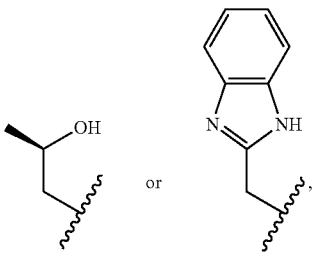

or wherein each R⁴ is; and iii) that when a Ni(II) cation is complexed with the macrocyclic core, the macrocyclic core does not have the following structure

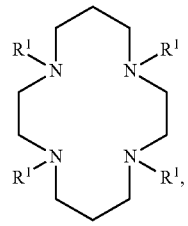

wherein each R¹ is

2. The macrocyclic compound of claim 1, wherein the macrocyclic core has the following structure:

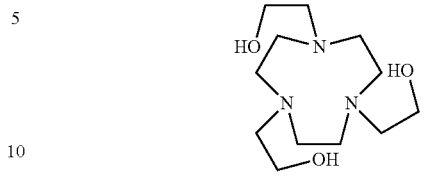

3. A composition comprising a compound of claim 1 and a pharmaceutically acceptable carrier.

4. A method to obtain an image of at least a portion of a cell, organ, vasculature, or tissue comprising the steps of:
  contacting the cell, organ, vasculature, or tissue with a compound of claim 1, and
  imaging at least a portion of the cell, organ, vasculature, or tissue to obtain an image of the portion of a cell, organ, vasculature, or tissue,
  wherein the image is obtained by using magnetic resonance.

5. The method of claim 4, wherein the cell, organ, vasculature, or tissue is part of an individual.

6. The method of claim 4, wherein the image is obtained using magnetic resonance imaging (MRI).

7. The method of claim 4, wherein the image is obtained using chemical exchange saturation transfer (CEST).

8. The method of claim 4, wherein the image is obtained using paramagnetic chemical exchange saturation transfer (paraCEST).

9. The method of claim 4, wherein the image is obtained using magnetic resonance spectroscopy imaging (MRSI).

10. The method of claim 4, wherein the image is obtained using thermometry.

11. The method of claim 4, wherein the image is obtained using pH mapping.

* * * * *